(12) United States Patent
Kobilka et al.

(10) Patent No.: US 11,370,879 B2
(45) Date of Patent: Jun. 28, 2022

(54) SOLUTION-PROCESSABLE INDENOFLUORENES AND METHODS TO GENERATE SOLUTION-PROCESSABLE INDENOFLUORENES

(71) Applicant: International Business Machines Corporation, Armonk, NY (US)

(72) Inventors: Brandon M. Kobilka, Tucson, AZ (US); Jacob T. Porter, Highland, NY (US); Scott B. King, Rochester, MN (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 123 days.

(21) Appl. No.: 16/220,069

(22) Filed: Dec. 14, 2018

(65) Prior Publication Data

US 2020/0190254 A1    Jun. 18, 2020

(51) Int. Cl.
*C08G 61/12* (2006.01)
*H01L 51/00* (2006.01)
(Continued)

(52) U.S. Cl.
CPC ............ *C08G 61/126* (2013.01); *C07C 13/70* (2013.01); *C07D 409/10* (2013.01);
(Continued)

(58) Field of Classification Search
CPC ............ H01L 51/0036; H01L 51/0039; H01L 51/0068; H01L 51/0055; H01L 51/0069;
(Continued)

(56) References Cited

U.S. PATENT DOCUMENTS 8,278,394 B2    10/2012  Pan et al.
8,507,901 B2    8/2013   Pan
(Continued)

FOREIGN PATENT DOCUMENTS

CN    107254032 A     10/2017
WO    2011159763 A1   12/2011
(Continued)

OTHER PUBLICATIONS

Hadizad et al, A General Synthetic Route to Indenofluorene Derivatives as New Organic Semiconductors, 2005, Organic Letters, vol. 7 No 5, 795-797. (Year: 2005).*

(Continued)

*Primary Examiner* — Andrew J Golden
(74) *Attorney, Agent, or Firm* — Patterson + Sheridan, LLP

(57) ABSTRACT

In an embodiment, a composition is provided that includes an indenofluorene moiety; an alkyl radical, an aryl radical, or a heteroaryl radical chemically bound to the indenofluorene moiety; and an electron donor moiety bound to the indenofluorene moiety. In another embodiment, a device is provided that includes compositions described herein. In another embodiment, a method of forming a donor-acceptor small molecule or a donor-acceptor copolymer is provided that includes forming an indenofluorene moiety; forming an electron donor moiety; and reacting the indenofluorene moiety with the electron donor moiety in a cross-coupling reaction.

20 Claims, 10 Drawing Sheets

(51) Int. Cl.
*C07C 13/70* (2006.01)
*C07D 513/04* (2006.01)
*C07D 409/10* (2006.01)
*C07D 495/04* (2006.01)

(52) U.S. Cl.
CPC ......... *C07D 495/04* (2013.01); *C07D 513/04* (2013.01); *H01L 51/0036* (2013.01); *H01L 51/0039* (2013.01); *H01L 51/0068* (2013.01); *H01L 51/0069* (2013.01); *H01L 51/0074* (2013.01); *C08G 2261/12* (2013.01); *C08G 2261/3243* (2013.01); *C08G 2261/3246* (2013.01); *C08G 2261/3247* (2013.01); *C08G 2261/411* (2013.01); *C08G 2261/414* (2013.01); *C08G 2261/91* (2013.01); *C08G 2261/95* (2013.01)

(58) Field of Classification Search
CPC .............................. C08G 61/126; C08G 61/02; C08G 2261/411; C08G 2261/414; C08G 2261/3142
See application file for complete search history.

(56) References Cited

U.S. PATENT DOCUMENTS

| | | | |
|---|---|---|---|
| 9,099,660 | B2 | 8/2015 | Haley et al. |
| 9,562,136 | B2 | 2/2017 | Humphries et al. |
| 9,728,724 | B2 | 8/2017 | Ludemann et al. |
| 9,828,544 | B2 | 11/2017 | Gu et al. |
| 2006/0046092 | A1 | 3/2006 | Towns et al. |
| 2009/0036643 | A1* | 2/2009 | Marks ................ C08G 61/126 528/380 |
| 2009/0149627 | A1 | 6/2009 | Pan et al. |
| 2009/0308456 | A1 | 12/2009 | Rand et al. |
| 2013/0053558 | A1 | 2/2013 | Pflumm et al. |
| 2013/0096336 | A1 | 4/2013 | Haley et al. |
| 2013/0150592 | A1 | 6/2013 | Haley et al. |
| 2014/0073753 | A1 | 3/2014 | Seferos et al. |
| 2015/0322208 | A1 | 11/2015 | Mitchell et al. |

FOREIGN PATENT DOCUMENTS

| | | |
|---|---|---|
| WO | 2014094954 A1 | 6/2014 |
| WO | 2015013656 A2 | 1/2015 |

OTHER PUBLICATIONS

STIC search results (Year: 2020).*
Lo et al, The synthesis, structure, and properties of 5,6,11,12-tetraarylindeno[1,2-b]fluorenes and their applications as donors for organic photovoltaic devices, 2017, Org. Chem. Front., 4, 675-681. (Year: 2017).*
Martinez, A theoretical study of substituted indeno[1,2-b]fluorene compounds and their possible applications in solar cells, Chemical Physics Letters 636 (2015) 31-34. (Year: 2015).*
Chase et al., "6,12-Diarylindeno[1,2-b]fluorenes: Syntheses, Photophysics, and Ambipolar OFETs," dx.doi.org/10.1021/ja303402p | J Am. Chem. Soc. 2012, 134, 10349-10352.
Nishida et al., "Synthesis, Crystal Structures, and Properties of 6,12-Diaryl-Substituted Indeno[1,2-b]fluorenes," Chemistry—A European Journal / vol. 18, Issue 29, Jun. 12, 2012 [Abstract Only].
Zhou et al., "Synthesis of Diacetylene Macrocycles Derived from 1,2-Diethynyl Benzene Derivatives: Structure and Reactivity of the Strained Cyclic Dimer," J. Org. Chem., 1994, 59 (6), pp. 1294-1301 DOI: 10.1021/jo00085a016 Publication Date: Mar. 1994 [Abstract Only].
Lo et al., "The Synthesis, Structure, and Properties of 5,6,11,12-tetraarylindeno[1,2-b]flouroenes and their Applications as Donors for Organic Photovoltaic Devices," Organic Chemistry Frontiers, Issue 5, 2017 [Abstract Only].
Chase et al, "Electron Accepting 6,12-Diethynylindeno[1,2-b]fluorenes: Crystal Structures, and Photophysical Properties," Sep. 26, 2011 https://doi.org/10.1002/anie.201104797 [Abstract Only].
List of IBM Patents or Patent Applications Treated as Related, for U.S. Appl. No. 16/220,069, filed Dec. 14, 2018.

* cited by examiner

SOLUTION-PROCESSABLE INDENOFLUORENES AND METHODS TO GENERATE SOLUTION-PROCESSABLE INDENOFLUORENES

BACKGROUND

The present disclosure relates to donor-acceptor organic semiconductors, and more specifically, to indenofluorenes useful for donor-acceptor organic semiconductors.

Conjugated polymers have found extensive use in organic semiconducting applications such as organic field-effect transistors, organic light-emitting diodes, and organic photovoltaic cells. These organic-based materials offer several advantages that their inorganic counterparts lack, including the ability to be solution processed into large-area thin-films and to be fabricated into lightweight, flexible devices as well as the capacity to have their properties tuned through synthesis. One method of modifying the optical and electronic properties of conjugated polymers is to synthesize materials comprised of alternating electron-donating ("donor") and electron-accepting moieties ("acceptor") in so called donor-acceptor copolymers or donor-acceptor small molecules.

However, these donor-acceptor copolymers and donor-acceptor small molecules suffer from solubility issues. Therefore, there is a need for solution processable donor-acceptor copolymers and donor-acceptor small molecules, and methods of making such compounds.

SUMMARY

In an embodiment is provided a composition that includes an indenofluorene moiety; an alkyl radical, an aryl radical, or a heteroaryl radical chemically bound to the indenofluorene moiety; and an electron donor moiety bound to the indenofluorene moiety.

In another embodiment is provided a device that includes compositions described herein.

In another embodiment is provided a method of forming a donor-acceptor small molecule that includes forming an indenofluorene moiety; forming an electron donor moiety; and reacting the indenofluorene moiety with the electron donor moiety in a coupling reaction.

In another embodiment is provided a method of forming a donor-acceptor copolymer that includes forming an indenofluorene moiety; forming an electron donor moiety; and reacting the indenofluorene moiety with the electron donor moiety in a cross-coupling reaction.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1A:
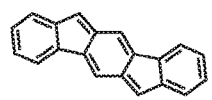
FIG. 1A shows an indenofluorene (IDF).

Embodiments described herein illustrate indenofluorene compounds useful for donor-acceptor organic semiconductors, and methods of forming such. The methods and materials described herein find use in a wide variety of organic semiconductor applications such as organic field-effect transistors (OFETs), organic light-emitting diodes (OLEDs), and organic photovoltaics (OPVs)

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Numbered chemical structures are numbered using numbers, or numbers and letters, in parentheses. Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s).

As used herein, the term "substituted" refers to a hydrogen group that has been replaced with a carbon atom, a heteroatom, or a heteroatom-containing group. For example, a "substituted hydrocarbyl" is a radical made of carbon and hydrogen where at least one hydrogen is replaced by a carbon atom, a heteroatom, or heteroatom-containing group.

The term "carbon substituted" refers to a substituted species where a hydrogen group has been replaced with a carbon atom.

The term "heterosubstituted" refers to a substituted species where a hydrogen group has been replaced with a heteroatom or heteroatom-containing group.

The following abbreviations may be used herein: TMS is trimethylsilyl, DMF (also referred to as dmf) is dimethylformamide, EtOH is ethanol, Me is methyl, Et is ethyl, Pr is propyl, cPr is cyclopropyl, nPr is normal propyl, iPr is isopropyl, Bu is butyl, nBu is normal butyl, iBu is isobutyl, sBu is sec-butyl, tBu is tert-butyl, p-tBu is para-tert-butyl, Ph is phenyl, Bn is benzyl (i.e., $CH_2Ph$), Oct is octyl, Cy is cyclohexyl, p-Me is para-methyl, THF (also referred to as thf) is tetrahydrofuran, PhMe is toluene.

Room temperature is between about 15° C. and 25° C. unless otherwise indicated.

As used herein, "alkoxy" includes those where the alkyl group is a $C_1$ to $C_{50}$ hydrocarbyl. The alkyl group may be straight chain, branched, or cyclic. The alkyl group may be saturated or unsaturated. In some embodiments, the alkyl group may include at least one aromatic group.

The terms "alkyl group," "alkyl radical," "alkyl," "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "alkyl group" refers to $C_1$-$C_{100}$ radicals, that may be linear, branched, or cyclic, and when cyclic, aromatic or non-aromatic. Examples of such radicals include methyl, ethyl, n-propyl, isopropyl, n-butyl, isobutyl, sec-butyl, tert-butyl, pentyl, iso-amyl, hexyl, octyl, cyclopropyl, cyclobutyl, cyclopentyl, cyclohexyl, cyclooctyl, and their substituted analogues. Substituted alkyl radicals are those in which at least one hydrogen atom of the hydrocarbyl radical has been substituted with at least one halogen (such as Br, Cl, F or I) or at least one functional group such as $C(O)R^*$, $C(O)NR^*_2$, $C(O)OR^*$, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, and $PbR^*_3$ (where $R^*$ is independently a hydrogen or hydrocarbyl radical, and two or more $R^*$ may join together to form a substituted or unsubstituted saturated, partially unsaturated or aromatic cyclic or polycyclic ring structure), or where at least one heteroatom has been inserted within a hydrocarbyl ring.

The term "alkenyl" or "alkenyl group" or "alkenyl radical" refers to a straight-chain, branched-chain, or cyclic hydrocarbon radical having one or more double bonds. These alkenyl radicals may be optionally substituted. Examples of suitable alkenyl radicals include ethenyl, propenyl, allyl, 1,4-butadienyl, cyclopropenyl, cyclobutenyl, cyclopentenyl, cyclohexenyl, cyclooctenyl, including their substituted analogues.

The term "alkoxy" or "alkoxy group" or "alkoxy radical" refers to a radical with an oxygen atom bonded to an organic group (e.g., an alkyl or aryl group) wherein the term alkyl is as defined above. Examples of alkoxy radicals include methoxy, ethoxy, n-propoxy, iso-propoxy, n-butoxy, isobutoxy, sec-butoxy, tert-butoxy, and phenoxy.

The term "aryl" or "aryl group" or "aryl radical" includes a $C_4$-$C_{60}$ aromatic ring, such as a $C_4$-$C_{20}$ aromatic ring, such as a six carbon aromatic ring, and substituted variants thereof, including phenyl, 2-methyl-phenyl, xylyl, and 4-bromo-xylyl. Likewise, heteroaryl refers to an aryl group where a ring carbon atom (or, e.g., two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxy, or aryl group exist (e.g., n-butyl, iso-butyl, sec-butyl, and tert-butyl) reference to one member of the group (e.g., n-butyl) is intended to include the remaining isomers (e.g., iso-butyl, sec-butyl, and tert-butyl) in the family, unless otherwise specified herein. Likewise, reference to an alkyl, alkenyl, alkoxy, or aryl group without specifying a particular isomer (e.g., butyl) includes all isomers (e.g., n-butyl, iso-butyl, sec-butyl, and tert-butyl).

For purposes of this disclosure, electron donor is used interchangeably with donor. For purposes of this disclosure, electron acceptor is used interchangeably with acceptor.

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan. In some embodiments, the compounds described herein can contain one or more chiral centers. Disclosure of such compounds, unless otherwise specified, includes racemic mixtures, diastereomers, enantiomers, and mixtures containing one or more stereoisomer. Further, unless otherwise specified, the disclosed compounds encompass racemic forms of the compounds in addition to individual stereoisomers, as well as mixtures containing any of these. The word "compound," as used herein, includes any chemical structure in which two or more chemical elements are bonded together. Thus, "compound" includes, but is not limited to, small molecules, cross-linkers, monofunctional molecules, monomers, and polymers.

The term "ring atom" refers to an atom that is part of a cyclic ring structure. By this definition, a benzyl group has six ring atoms and tetrahydrofuran has five ring atoms. A heterocyclic ring is a ring having a heteroatom in the ring structure (i.e., one of the ring atoms is a heteroatom) as opposed to a heteroatom-substituted ring where a ring atom is bonded to a heteroatom that is not a ring atom. For example, tetrahydrofuran is a heterocyclic ring and 4-N,N-dimethylamino-phenyl is a heteroatom-substituted ring.

Important factors in the design of donor-acceptor small molecules and polymers include appropriately adjusted highest occupied molecular orbital (HOMO) and lowest unoccupied molecular orbital (LUMO) energy levels, a reasonably narrow band gap, high charge carrier mobilities, and optimal active layer morphologies. However, the choice of donor materials is abundant relative to that of novel acceptor materials. One major reason for this is the difficulty associated with synthesizing stable acceptor materials that also possess solubilizing side chains. One highly promising material that has yet to be incorporated into donor-acceptor organic semiconductors is indenofluorene.

FIG. 1A shows an indenofluorene (IDF) 101, which is a 6-5-5-6 fused ring system. IDFs have two fewer carbons and π-electrons than expected for conjugated materials, making it formally anti-aromatic with a central quinoid structure (as opposed to a benzoid structure). This quinoid structure not only leads to materials with low energy band gaps (absorbing more of the red and near-IR regions which often go underutilized in organic solar cells), it also enhances the singlet biradical character associated which the molecule. Molecules that possess singlet biradicals tend to have low lying triplet excited states. Triplet states have much longer lifetimes than singlet states, which are advantageous for semiconductor applications as it allows for longer lived charge carriers or excited electron-hole pairs (excitons), which can travel longer distances within an active layer. This results in a greater internal conversion efficiency (the conversion of photon to separated charges that generate current). Due to the lack of solution-processable materials of this nature, indenofluorenes and modified indenofluorenes have not seen wide-spread use in organic semiconducting devices.

In embodiments described herein, the indenofluorene is modified to form a solution-processable acceptor compounds that also possess solubilizing side chains. The indenofluorene and similar compounds are electron acceptors (also known as acceptor compounds). This acceptor compound can then be reacted with a donor compound to form donor-acceptor copolymers and donor-acceptor small molecules. These donor-acceptor copolymers and donor-acceptor small molecules, having solubilizing hydrocarbon side chains, can then be used for solution-processable organic semiconducting devices based on donor-acceptor materials.

Figure 1B:
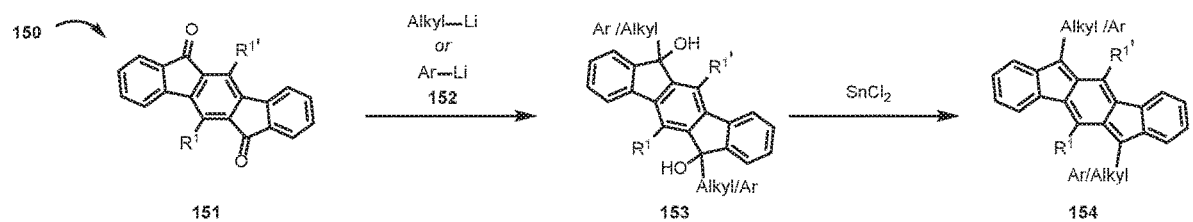
FIG. 1B is a chemical reaction diagram illustrating a general method of forming an IDF according to some embodiments.

FIG. 1B illustrates a general method 150 of starting with an indenofluorenedione 151 having a central benzoid structure to form an indenofluorene 154 having a central quinodimethane structure according to some embodiments. In the general method 150, the indenofluorene 154 is formed by a nucleophilic addition of, e.g., an alkyl-lithium or an aryl-lithium 152 to the ketone of indenofluorenedione 151 followed by a tin (II) chloride (SnCl$_2$) reduction of an intermediate di-hydroxy compound 153. In some embodiments, each of R$^1$ and R$^{1'}$ is independently a hydrogen, an alkyl (substituted or unsubstituted), an alkoxy, an aryl (substituted or unsubstituted), and heteroaryl (substituted or unsubstituted). In some embodiments, the alkyl-lithium/aryl-lithium can be the same or different alkyl-lithium/aryl-lithium (denoted by Alkyl, Alkyl', Ar, and Ar') depending on the application. In some embodiments, each of Alkyl and Alkyl' of the alkyl-lithium 152 is an alkyne moiety. In some embodiments, the Ar and Ar' is an aryl moiety or a heteroaryl moiety. Each of R$^1$, R$^{1'}$, Alkyl, Alkyl', Ar, and Ar' are further described below.

The various reaction pathways herein highlight several routes to new compositions of matter (e.g., molecules) in the indenofluorene space. These molecules possess alkyl chains and terminal aryl halides that allow for their usage as building blocks in solution-processable polymers for organic semiconductors. The numerous unique compositions of matter enable multiple different configurations of side chains (e.g., alkyl, aryl, and heterorayl), as well as a variety of different pathways to achieve the desired configurations.

Donor-Acceptor Small Molecules and Copolymers

According to some embodiments, a donor-acceptor small molecule represented by the formula D-A-D' is provided. In some embodiments, A is an indenofluorene moiety or modified indenofluorene moiety. In some embodiments, D-A-D' is represented by formula (I)

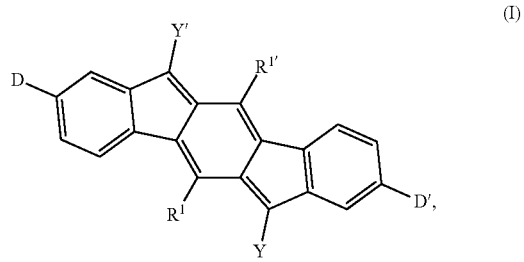

wherein:
each of Y and Y' is independently an alkyl radical (such as a C$_1$ to C$_{50}$ alkyl radical, such as a C$_1$ to C$_{20}$ alkyl radical, for example a C$_1$ to C$_8$ alkyl radical), a substituted alkyl radical (such as a C$_1$ to C$_{50}$ substituted alkyl radical, such as a C$_1$ to C$_{20}$ substituted alkyl radical, for example a C$_1$ to C$_8$ substituted alkyl radical), an unsubstituted aryl radical (such as a C$_4$ to C$_{20}$ unsubstituted aryl ring, such as a C$_6$ to C$_{14}$ unsubstituted aryl ring), a substituted aryl radical (such as a C$_4$ to C$_{20}$ substituted aryl ring, such as a C$_6$ to C$_{14}$ substituted aryl ring), an unsubstituted heteroaryl radical (such as a C$_4$ to C$_{20}$ unsubstituted heteroaryl ring, such as a C$_6$ to C$_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring);

each of $R^1$ and $R^{1'}$ is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring); and each of D and D' comprises an electron donor moiety (such as a thiophene moiety, including any thiophene moiety described herein). D and D' may be the same or different.

In some embodiments, D and/or D' is an electron donor moiety, such as a thiophene represented by formula (IIa):

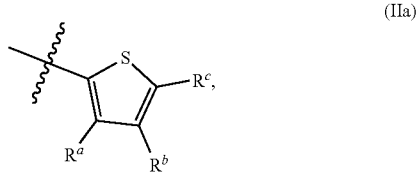

(IIa)

wherein:

the wavy bond denotes a connection to the indenofluorene moiety;

each of $R^a$, $R^b$, and $R^c$ is independently a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), a substituted heteroaryl radical (such as a $C_4$ to $C_{20}$ substituted heteroaryl ring, such as a $C_6$ to $C_{14}$ substituted heteroaryl ring), or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

In some embodiments, D and/or D' is an electron donor moiety, such as a thiophene represented by formula (IIb):

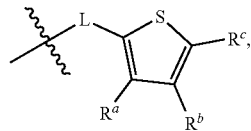

wherein:

the wavy bond denotes a connection to the indenofluorene moiety;

L includes at least one carbon atom;

each of $R^a$, $R^b$, and $R^c$ is independently a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), a substituted heteroaryl radical (such as a $C_4$ to $C_{20}$ substituted heteroaryl ring, such as a $C_6$ to $C_{14}$ substituted heteroaryl ring), or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

In some embodiments, D and/or D' is an electron donor moiety, such as a thiophene represented by formula (IIc):

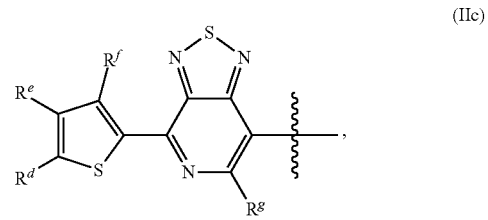

(IIc)

wherein:

the wavy bond denotes a connection to the indenofluorene moiety;

each of $R^d$, $R^e$, and $R^f$ is independently a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring), or one or more of $R^d$ and $R^e$ and $R^e$ and $R^f$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring; and $R^g$ is a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical or for example a perfluorinated alkyl, an ester, or an amide), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring), or one or more of $R^d$ and $R^e$ and $R^e$ and $R^f$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

In some embodiments, the donor compound (e.g., a p-type semiconductor material, molecule, or polymer) can be a "donor/acceptor" compound which refers to the donor compound having both electron acceptor characteristics and electron donor characteristics, as shown by formula IIc.

Additional examples of electron donor moieties include

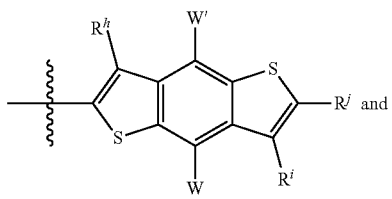

(IId)

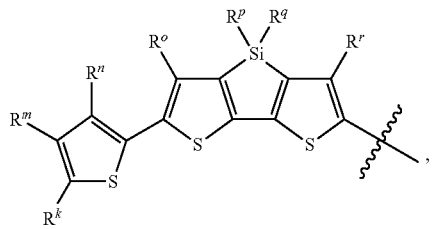

(IIe)

wherein:

the wavy bond denotes a connection to the indenofluorene moiety;

when W and W' is present, each of W and W' is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring);

when $R^h$, $R^i$, and $R^j$ is present, each of $R^h$, $R^i$, and $R^j$ is independently a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring), or $R^i$ and $R^j$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring; and when $R^k$, $R^m$, $R^n$, $R^o$, $R^p$, $R^q$, and $R^r$ is present, each of $R^k$, $R^m$, $R^n$, $R^o$, $R^p$, $R^q$, and $R^r$ is independently a hydrogen, a halogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring), or one or more of $R^k$ and $R^m$, $R^m$ and $R^n$, or $R^p$ and $R^q$ is joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

According to some embodiments, a donor-acceptor copolymer is represented by formula (III)

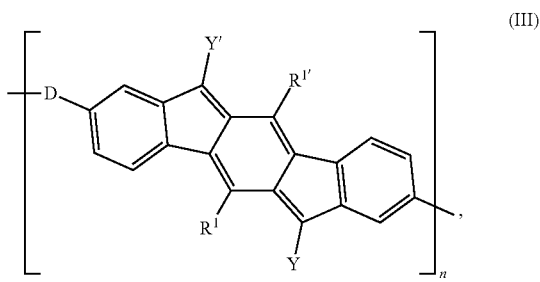

wherein:
each of Y and Y' is independently an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring);
each of $R^1$ and $R^{1'}$ is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring);
n is an integer from 1 to 1,000,000 (such as from about 1 to 100,000, such as from about 1 to 1,000, such as from about 1 to 100, such as from about 8 to about 100, such as from about 8 to about 50, such as from about 8 to about 20); and
D comprises an electron donor moiety (such as a thiophene moiety, including any thiophene moiety described herein).

Synthesis of the various acceptor compounds, donor-acceptor small molecules, and donor-acceptor copolymers are described below. For the syntheses and molecules shown below, varied substitution about the various acceptor compounds, donor-acceptor small molecules, and donor-acceptor copolymers is contemplated. Such modifications, if desired, can be achieved by methods known to those of skill in the art.

Synthesis of Acceptor Compounds

Figure 2A:
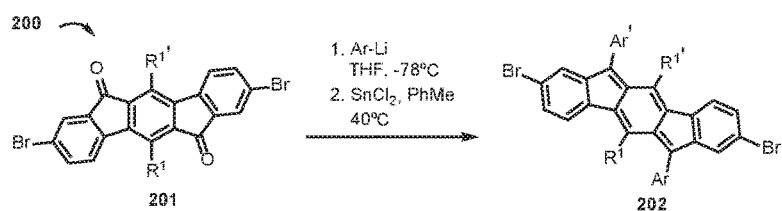
FIG. 2A is a chemical reaction diagram illustrating a method of forming an aryl-functionalized (or heteroaryl-functionalized) acceptor compound according to some embodiments.

FIG. 2A illustrates a method 200 of forming an aryl-functionalized (or heteroaryl-functionalized) acceptor compound 202 from a dione 201 according to some embodiments. Formation of the aryl-functionalized acceptor compound 202 includes a nucleophilic addition an aryl (or heteroaryl) lithiate, made in situ, followed by a tin chloride reduction. By controlling the stoichiometry of the reaction, aryl groups can be added such that Ar and Ar' can be the same or different groups. The aryl-functionalized acceptor compound 202 is an aryl-functionalized IDF, wherein each of Ar and Ar' is independently an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring); and
each of $R^1$ and $R^{1'}$ is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring). The aryl-functionalized acceptor compound 202 can be used to synthesize conjugated donor-acceptor copolymers and donor-acceptor small molecules, or can be further modified as described herein.

Figure 2B:
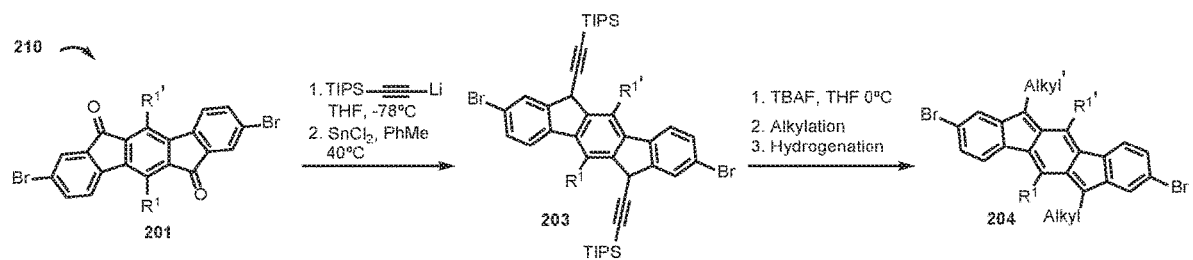
FIG. 2B is a chemical reaction diagram illustrating a method of forming an alkyl-functionalized acceptor compound according to some embodiments.

FIG. 2B illustrates a method 210 of forming an alkyl-functionalized acceptor compound 204 from the dione 201 according to some embodiments. The alkyl-functionalized acceptor compound 204 is an alkyl-functionalized IDF. Formation of the alkyl-functionalized acceptor compound 204 includes a nucleophilic addition of a triisopropylsilyl ether (TIPS) substituted alkynyl lithiate (made in situ) followed by a reduction to give a di-alkyne compound 203. The di-alkyne compound 203 is then transformed to the alkyl-functionalized acceptor compound 204 by the following operations: removal of the TIPS protecting group by using, e.g., tetrabutyl ammonium fluoride (TBAF), to provide a terminal alkyne (a deprotection operation), an alkylation of the terminal alkyne, and a subsequent hydrogenation. By controlling the stoichiometry of the various reactions, alkyl groups can be added such that Alkyl and Alkyl' can be the same or different groups. If present in 201, 203, and 204, $R^1$ and $R^{1'}$ are defined above; and each of Alkyl and Alkyl' is independently an alkyl radical (such as a $C_1$ to $C_{50}$ alkyl radical, such as a $C_1$ to $C_{20}$ alkyl radical, for example a $C_1$ to $C_8$ alkyl radical), or a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical).

The alkylation of the terminal alkyne may be performed by using a substituted or unsubstituted, cyclic or acyclic, hydrocarbyl halide (e.g., 1-iodopentane). The hydrogenation operation may be performed using hydrogen gas (directly from a cylinder or generated by the oxidation of cyclohexene to benzene) with a palladium on carbon (Pd/C) catalyst at ambient temperature/pressure or under high pressure or elevated temperature using a Parr bomb or similar style reactor. The hydrogenation may also be performed using a flow-process reactor, such as an H-Cube reactor or similar technology. The alkyl-functionalized acceptor compound 204 can be used to synthesize conjugated donor-acceptor copolymers and donor-acceptor small molecules, or can be further modified as described herein.

Figure 2C:
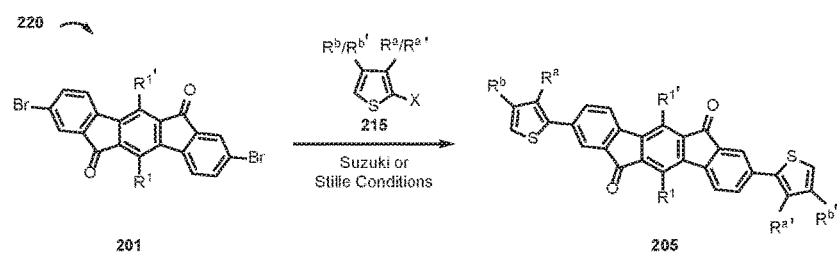
FIG. 2C is a chemical reaction diagram illustrating a method of forming a dithiophene via a Suzuki cross-coupling reaction or a Stille cross-coupling reaction according to some embodiments.

FIG. 2C shows a method 220 of forming a dithiophene 205 via a Suzuki cross-coupling reaction and/or a Stille cross-coupling reaction according to some embodiments. The cross-coupling reactions occur between a thiophene 215 and the dione 201. By controlling the stoichiometry of the cross-coupling reactions, thiophenes can be added such that $R^a$, $R^{a'}$, $R^b$, and $R^{b'}$ can be the same or different groups. If present in 201 and 205, $R^1$ and $R^{1'}$ are defined above; and each of $R^a$, $R^{a'}$, $R^b$, and $R^{b'}$ is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring), or one or more of $R^a$ and $R^b$, and $R^{a'}$ and $R^{b'}$ are joined to form a saturated cyclic ring, a substituted saturated cyclic ring, an unsubstituted unsaturated cyclic ring, or a substituted saturated cyclic ring. The thiophene 215 includes functionalization "X", where X is, e.g., a boronic acid or a boronic ester for Suzuki cross-coupling reactions (e.g., a pinacol borate), or a trialkyl stannane (e.g., trimethylstannane) for Stille cross-coupling reactions; and $R^a$, $R^{a'}$, $R^b$, and $R^{b'}$ are defined above.

Figure 2D:
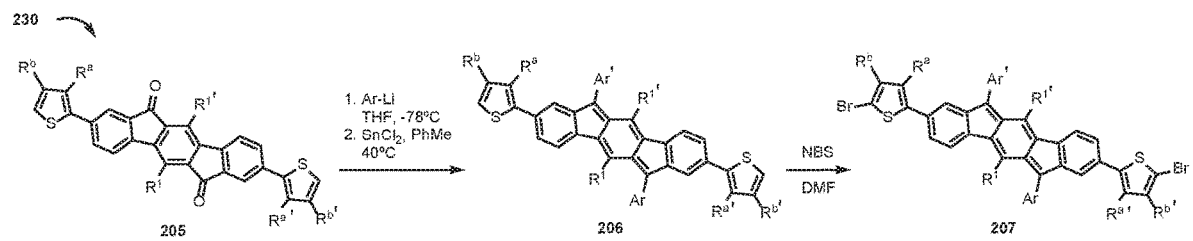
FIG. 2D is a chemical reaction diagram illustrating a method of forming an aryl-functionalized acceptor compound according to some embodiments.

FIG. 2D shows a method 230 of forming an aryl-functionalized acceptor compound 207 from the dithiophene 205 according to some embodiments. Formation of the di-aryl compound 206 is achieved by a nucleophilic addition of an aryl (or heteroaryl) lithiate (Ar—Li) and a tin chloride reduction, as described above. Bromination of the di-aryl compound 206 using N-bromosuccinimide (NBS) then forms the aryl-functionalized acceptor compound 207. By controlling the stoichiometry of the nucleophilic addition of the aryl (or heteroaryl) lithiate, Ar and Ar' can be the same or different groups. If present in 205-207, each of Ar, Ar', $R^1$, $R^{1'}$, $R^a$, $R^{a'}$, $R^b$, and $R^{b'}$ are defined above. In some embodiments, elemental bromine can be used to brominate di-aryl compound 206 in a procedure similar to that described below with respect to synthesizing acceptor compound 403. The aryl-functionalized acceptor compound 207 can be used to synthesize conjugated donor-acceptor copolymers and donor-acceptor small molecules as described herein.

Figure 2E:
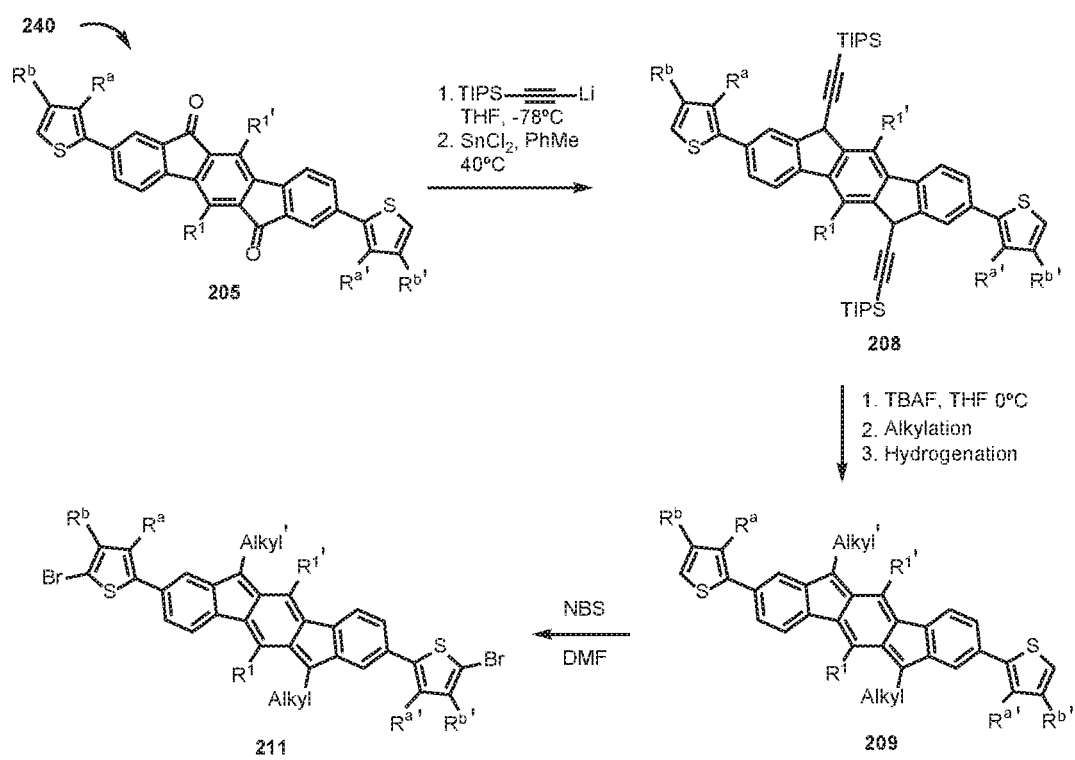
FIG. 2E is a chemical reaction diagram illustrating a method of forming an alkyl-functionalized acceptor compound according to some embodiments.

FIG. 2E shows a method 240 of forming an alkyl-functionalized acceptor compound 211 from the dithiophene 205 according to some embodiments. Formation of a di-alkyne 208 may be achieved by nucleophilic addition of an alkynyl lithiate and a tin chloride reduction as described above. A di-alkyl compound 209 is then formed from the di-alkyne 208 by the following operations: a removal of the TIPS protecting group using TBAF to provide a terminal alkyne, alkylation of the terminal alkyne, and subsequent hydrogenation in a manner similar to the procedures described above. By controlling the stoichiometry of the alkylation reaction, Alkyl and Alkyl' can be the same or different groups. Subsequent bromination of the di-alkyl compound 209 using NBS then provides the alkyl-functionalized acceptor compound 211. The bromination operation may be performed in a manner similar to the procedure described above. If present in 205, 208-209, and 211, each of Alkyl, Alkyl', $R^1$, $R^{1'}$, $R^a$, $R^{a'}$, $R^b$, and $R^{b'}$ are defined above. The alkyl-functionalized acceptor compound 211 can be used to synthesize conjugated donor-acceptor copolymers and donor-acceptor small molecules as described herein.

Figure 5A:
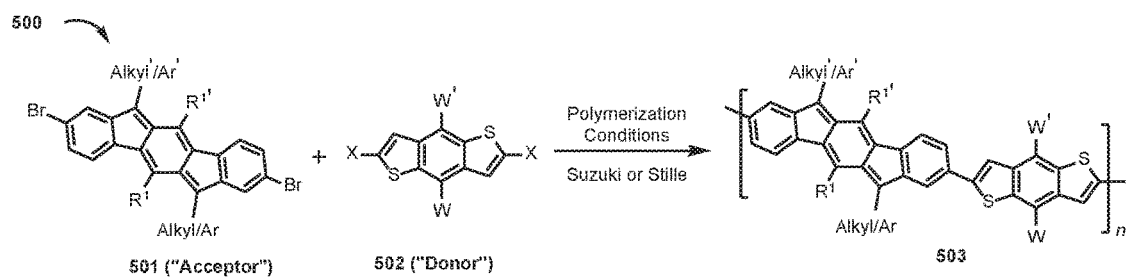
FIG. 5A is a chemical reaction diagram illustrating a general method of forming a donor-acceptor copolymer according to some embodiments.
Figure 5B:
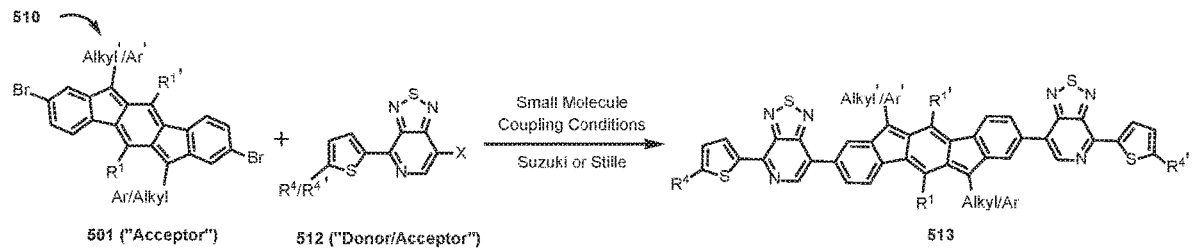
FIG. 5B is a chemical reaction diagram illustrating a general method of forming a donor-acceptor small molecule according to some embodiments.
Figure 5C:
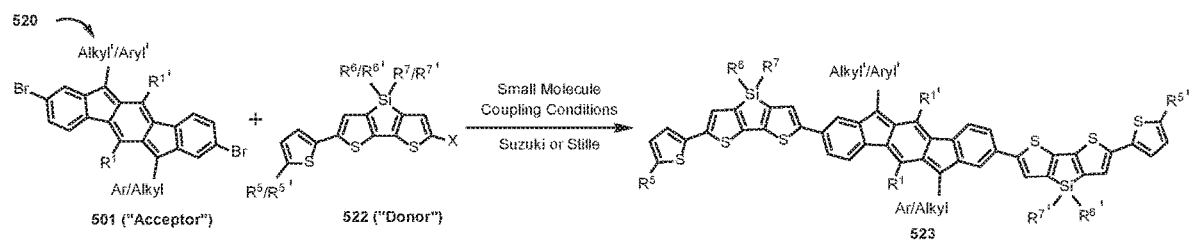
FIG. 5C is a chemical reaction diagram illustrating a general method of forming a donor-acceptor small molecule according to some embodiments.

While the di-aryl compound 206 and the di-alkyl compound 209 can be used as donor-acceptor small molecules, adding an additional donor moiety as shown in FIGS. 5A-5C (following bromination and cross-coupling) has unanticipated advantages. Thiophene does not have as high-lying of a HOMO level relative to other donors such as the silolodithiophenes (DTS, e.g., 522) and the benzodithiophenes (BDT, e.g., 502)), so incorporating donors like 502 and 522 into both polymers and small molecules could be used to raise the HOMO level and narrow the HOMO-LUMO band gap more than thiophene. It is noted that thiophenes ensure good reactivity to Pd-catalyzed cross-coupling reactions.

Figure 3A:
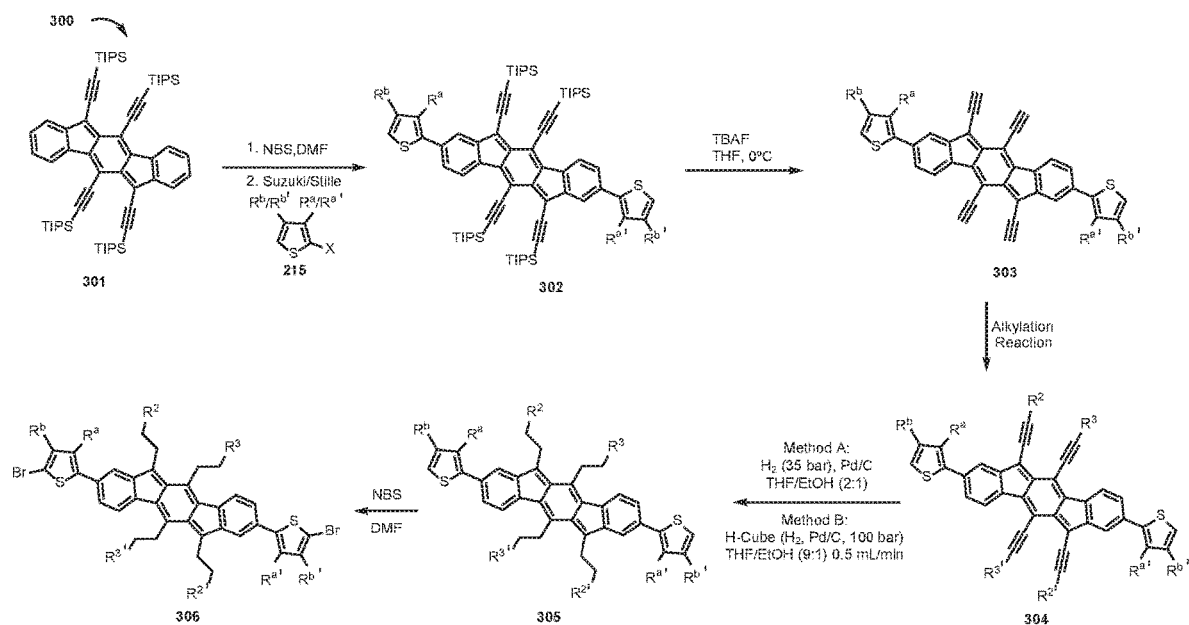
FIG. 3A is a chemical reaction diagram illustrating a method of forming an alkyl-functionalized acceptor compound according to some embodiments.

FIG. 3A illustrates a method 300 of forming an alkyl-functionalized acceptor compound 306 from a tetrakis-TIPS alkynyl indenofluorene 301 according to some embodiments. The tetrakis-TIPS alkynyl indenofluorene 301 is synthesized by procedures known in the art. The tetrakis-TIPS alkynyl indenofluorene 301 is brominated using NBS and coupled to thiophene 215 by a Suzuki cross-coupling reaction or a Stille cross-coupling reaction to form a dithiophene 302 in a manner similar to the procedures described above. By controlling the stoichiometry of the cross-coupling reaction, thiophenes can be added such that $R^a$, $R^{a'}$, $R^b$, and $R^{b'}$ can be the same or different groups. Subsequent deprotection using TBAF provides a terminal alkyne 303. The terminal alkyne 303 is alkylated to form a tetra-alkyne compound 304. The tetra-alkyne compound 304 is transformed to the alkyl-functionalized acceptor compound 306, proceeding through a tetra-alkylated compound 305, by a hydrogenation operation and a bromination operation. The deprotection, alkylation, hydrogenation, and bromination operations are performed in a manner similar to the procedures described above. If present in 302-306, each of $R^a$, $R^{a'}$, $R^b$, and $R^{b'}$ are defined above; and each of $R^2$, $R^{2'}$, $R^3$, and $R^{3'}$ is independently an alkyl radical (such as a $C_1$ to $C_{50}$ alkyl radical, such as a $C_1$ to $C_{20}$ alkyl radical, for example a $C_1$ to $C_8$ alkyl radical) or a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical). The alkyl-functionalized acceptor compound 306 can be used to synthesize conjugated donor-acceptor copolymers and donor-acceptor small molecules as described herein.

Figure 3B:
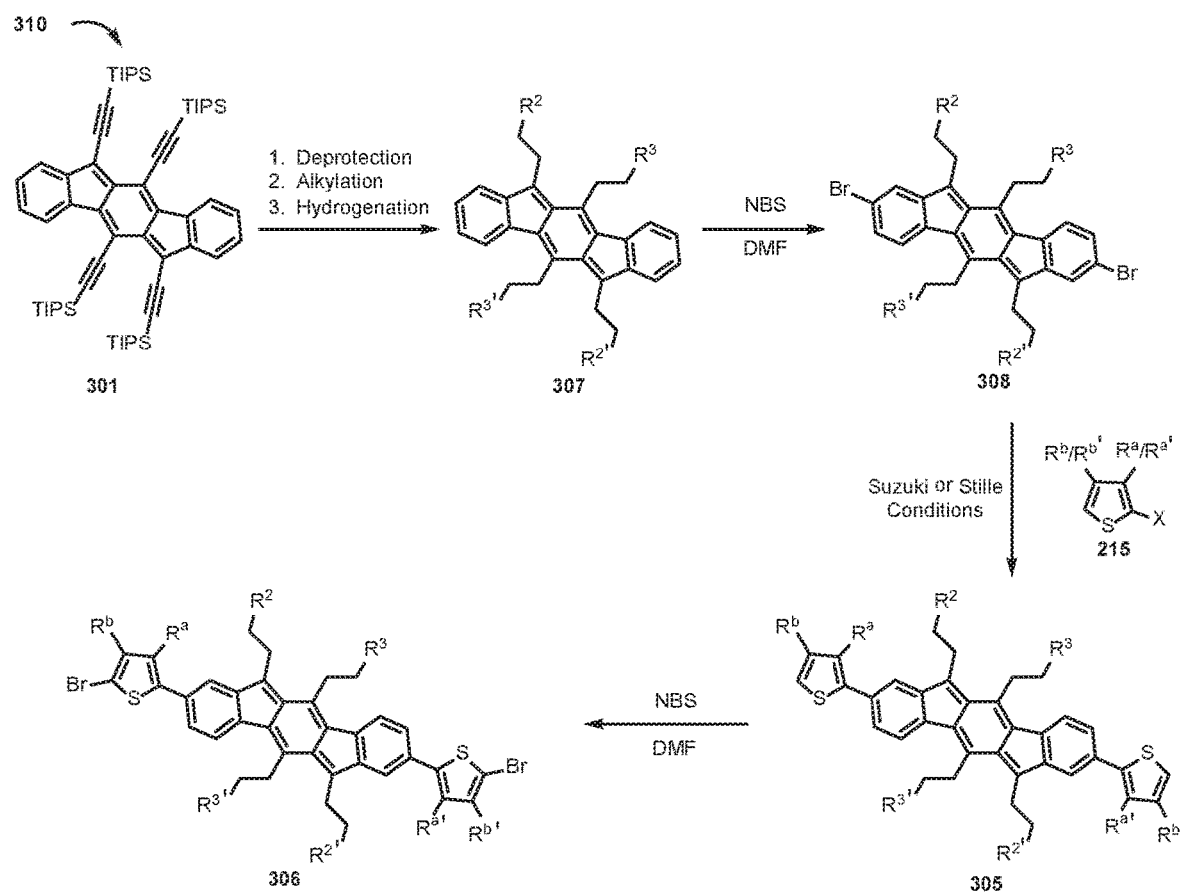
FIG. 3B is a chemical reaction diagram illustrating a method of forming an alkyl-functionalized acceptor compound according to some embodiments.

FIG. 3B illustrates a method 310 of forming an alkyl-functionalized acceptor compound 306 from a tetrakis-TIPS alkynyl indenofluorene 301 according to some embodiments. Method 310 is different from method 300. The tetrakis-TIPS alkynyl indenofluorene 301 is deprotected using TBAF. A subsequent alkylation operation and a hydrogenation operation provides a tetra-alkyl compound 307. By controlling the stoichiometry of the alkylation reaction, each of $R^2$, $R^{2'}$, $R^3$, and $R^{3'}$ can be the same or different groups. Bromination of the tetra-alkyl compound 307 using NBS then provides a di-bromo compound 308. The deprotection, alkylation, hydrogenation, and bromination operations are performed in a manner similar to the procedures described above. In some embodiments, elemental bromine can be used to brominate tetra-alkyl compound 307 in a procedure similar to that described below with respect to synthesizing acceptor compound 403. It should be noted that di-bromo compound 308 can be used to synthesize conjugated donor-acceptor copolymers and donor-acceptor small molecules as described herein.

The di-bromo compound 308 undergoes a Suzuki cross-coupling reaction or Stille cross-coupling reaction to form a tetra-alkylated compound 305 in a manner similar to the procedures described above. By controlling the stoichiometry of the cross-coupling reaction, thiophenes can be added such that $R^a$, $R^{a'}$, $R^b$, and $R^{b'}$ can be the same or different groups. Subsequent bromination of the tetra-alkylated compound 305 in a manner similar to the procedures described above then provides the alkyl-functionalized acceptor compound 306. Thiophene 215 includes functionalization "X", where X is, e.g., a boronic acid or a boronic ester for Suzuki cross-coupling reactions (e.g., a pinacol borate), or a trialkyl stannane (e.g., trimethylstannane) for Stille cross-coupling reactions. If present in 215 and 305-308, each of $R^a$, $R^{a'}$, $R^b$, $R^{b'}$, $R^2$, $R^{2'}$, $R^3$, and $R^{3'}$ is defined above. The alkyl-functionalized acceptor compound 306 can be used to synthesize conjugated donor-acceptor copolymers and donor-acceptor small molecules as described herein.

Figure 4A:
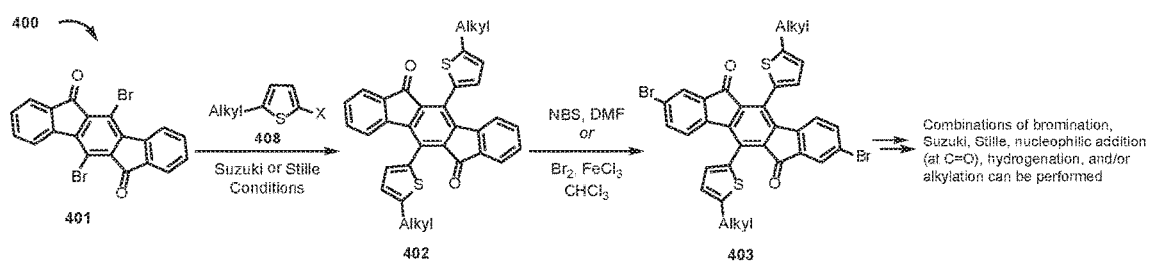
FIG. 4A is a chemical reaction diagram illustrating a method of forming an acceptor compound having heteroaryl moieties chemically connected to the central ring of the IDF according to some embodiments according to some embodiments.

FIG. 4A illustrates a method 400 of forming an acceptor compound 403 having heteroaryl moieties chemically connected to the central ring of the IDF according to some embodiments. The di-bromo-dione compound 401 undergoes a Suzuki or Stille cross-coupling reaction with an alkyl thiophene 408 to form a dithiophene 402 in a manner similar to the procedures described above. The alkyl thiophene 408 includes functionalization "X", where X is, e.g., a boronic acid or a boronic ester for a Suzuki cross-coupling reaction (e.g., a pinacol borate), or a trialkyl stannane (e.g., trimethylstannane) for a Stille cross-coupling reaction; and $R^a$, $R^{a'}$, $R^b$, and $R^{b'}$ are defined above. By controlling the stoichiometry of the cross-coupling reaction, thiophenes can be added such that Alkyl and Alkyl' can be the same or different groups. In some embodiments, a subsequent bromination operation using NBS is then performed to form the acceptor compound 403. Alternately, and in some embodiments, the bromination operation is a Lewis acid-catalyzed electrophilic aromatic substitution using liquid bromine and a Lewis acid (e.g., iron (III) chloride, $FeCl_3$). For compounds 401-403 and 408, each of Alkyl and Alkyl' is defined above.

Figure 4B:
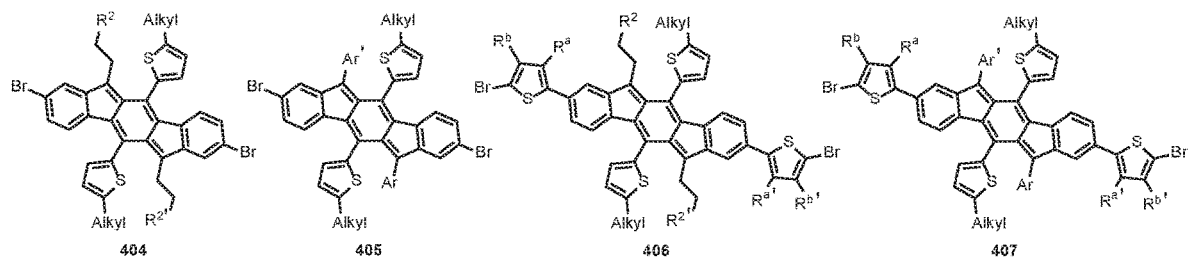
FIG. 4B shows example acceptor compounds having heteroaryl moieties chemically connected to the central ring of the IDF according to some embodiments.

In some embodiments, the acceptor compound 403 (having heteroaryl moieties chemically connected to the central ring of the IDF) can be used to synthesize conjugated donor-acceptor copolymers and donor-acceptor small molecules as described herein. Alternately, and in some embodiments, the acceptor compound 403 can be modified to form various acceptor compounds 404-407 as shown in FIGS. 4A and 4B. The various acceptor compounds 404-407 having heteroaryl moieties chemically connected to the central ring of the IDF may be formed by combinations of bromination, Suzuki cross-coupling, Stille cross-coupling, deprotection, nucleophilic addition of an aryl lithiate or alkynyl lithiate (at C=O), hydrogenation, and/or alkylation. Such reactions may be performed in a manner similar to the procedures described above. If present in 404-407, each of Alkyl, Alkyl', $R^a$, $R^{a'}$, $R^b$, $R^{b'}$, $R^2$, and $R^{2'}$ is defined above. The acceptor compounds 404-407 (having heteroaryl moieties chemically connected to the central ring of the IDF) can be used to synthesize conjugated donor-acceptor copolymers and donor-acceptor small molecules as described herein.

Figure 4C:
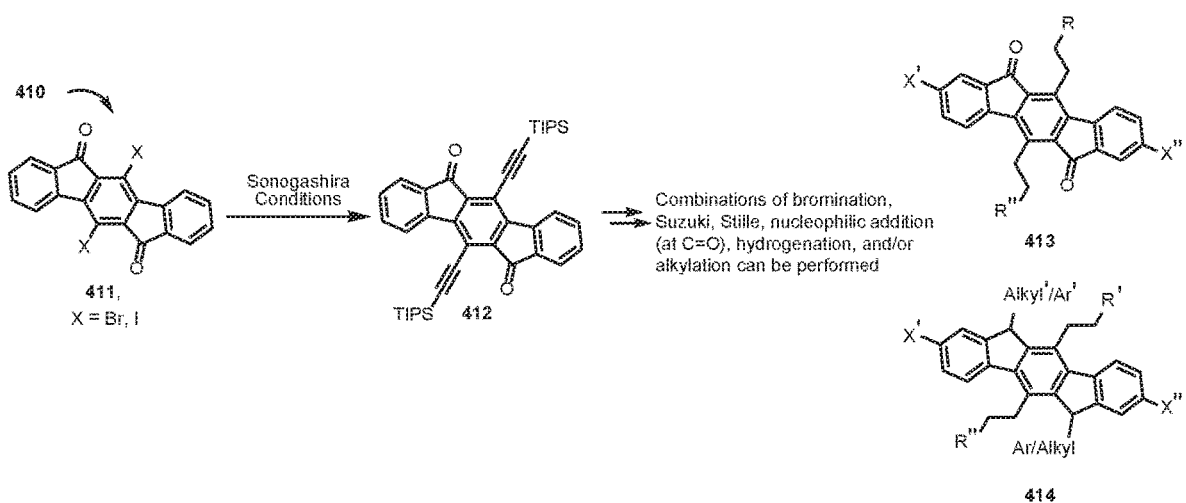
FIG. 4C is a chemical reaction diagram illustrating a method of forming various acceptor compounds according to some embodiments.

FIG. 4C illustrates a method 410 of forming various acceptor compounds 413-414 having alkyl moieties (R' and R") chemically connected to the central ring group from a known dione 411 (X=Br or I) according to some embodiments. In an embodiment, a Sonogashira cross-coupling utilizes (triisopropylsilyl)acetylene to form the bis-TIPS alkynyl indenofluorene 412.

The bis-TIPS alkynyl indenofluorene 412 is then modified to form various acceptor compounds 413-414. The various acceptor compounds 413-414 may be formed by combinations of bromination, Suzuki cross-coupling, Stille cross-coupling, deprotection, nucleophilic addition of an aryl lithiate or alkynyl lithiate (at C=O), hydrogenation, and/or alkylation. Such reactions may be performed in a manner similar to the procedures described above. If present in 412-414, each of Alkyl, Alkyl', Ar, and Ar' is defined above; each of R' and R" is independently an alkyl radical (such as a $C_1$ to $C_{50}$ alkyl radical, such as a $C_1$ to $C_{20}$ alkyl radical, for example a $C_1$ to $C_8$ alkyl radical), or a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical); and each of X' and X" is independently Br or a thiophene moiety, including any thiophene moiety described herein. The acceptor compounds 413-414 can be used to synthesize conjugated donor-acceptor copolymers and donor-acceptor small molecules as described herein.

Figure 4D:
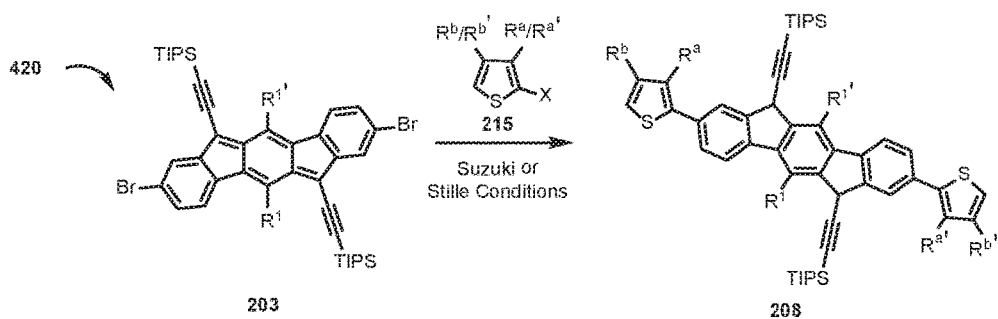
FIG. 4D is a chemical reaction diagram illustrating a method of forming a di-alkyne compound according to some embodiments.

FIG. 4D illustrates a method 420 of forming a di-alkyne compound 208 according to some embodiments. The method 420 utilizes a Suzuki cross-coupling or Stille cross-coupling reaction between the di-alkyne compound 203 and the thiophene 215. The thiophene 215 includes functionalization "X", where X is, e.g., a boronic acid or a boronic ester for Suzuki cross-coupling reactions (e.g., a pinacol borate), or a trialkyl stannane (e.g., trimethylstannane) for Stille cross-coupling reactions. The cross-coupling reactions may be performed in a manner similar to the procedures described above. By controlling the stoichiometry of the cross-coupling reaction, thiophenes can be added such that $R^a$, $R^{a'}$, $R^b$, and $R^{b'}$ can be the same or different groups. If present in 203, 208, and 215, each of $R^a$, $R^{a'}$, $R^b$, $R^{b'}$, $R^1$ and $R^{1'}$ is defined above. The di-alkyne compound 208 is then transformed to the alkyl-functionalized acceptor compound 211 by a deprotection, alkylation, hydrogenation, and bromination, in procedures similar to those described above.

Exemplary Donor Compounds

Donor compounds useful for embodiments described herein include, e.g., thiophene and thiophene derivatives such as 2,5-dibromothieno[3,2-b]thiophene and/or derivatives thereof; 2,5-dibromo-3,4-ethylenedioxythiophene and/or derivatives thereof; thieno[2,3-b]thiophene and/or derivatives thereof; thieno[3,2-b]thiophene and/or derivatives thereof; 3,4-ethylenedioxythiophene and/or derivatives thereof; 3,4-ethylenedithiothiophene and/or derivatives thereof; 3,4-dimethoxythiophene and/or derivatives thereof; 3,4-propylenedioxythiophene and/or derivatives thereof; hydroxymethyl EDOT and/or derivatives thereof; 2,6-dibromodithieno[3,2-b:2',3'-d]thiophene and/or derivatives thereof; 3,3',5,5'-tetrabromo-2,2'-bithiophene and/or derivatives thereof; 5,5'-dibromo-2,2'-bithiophene and/or derivatives thereof; 5,5'-diiodo-2,2'-bithiophene and/or derivatives thereof; dithieno[3,2-b:2',3'-d]thiophene and/or derivatives thereof; 2,2'-bithiophene and/or derivatives thereof; 2,3'-bithiophene and/or derivatives thereof; 2,5-dibromo-3-butylthiophene and/or derivatives thereof; 3,4-(2,2-dimethylpropylenedioxy)thiophene and/or derivatives thereof; 3-phenylthiophene and/or derivatives thereof; 2,5-dibromo-3-cyclohexylthiophene and/or derivatives thereof; 2,5-dibromo-3-hexylthiophene and/or derivatives thereof; thiophene-2-boronic acid pinacol ester and/or derivatives thereof; 2-bromo-3-hexylthiophene and/or derivatives thereof; 5-bromo-2-hexylthiophene and/or derivatives thereof; 2,5-bis(trimethylstannyl)thiophene and/or derivatives thereof; 3,4-(2',2'-diethylpropylene)dioxythiophene and/or derivatives thereof; 5,5''-dibromo-2,2':5',2''-terthiophene and/or derivatives thereof; 2,2'-bithieno[3,2-b]thiophene and/or derivatives thereof; 2,2':5',2''-terthiophene and/or derivatives thereof; 2,5-dibromo-3-(2-ethylhexyl)thiophene and/or derivatives thereof; 2,5-dibromo-3-octylthiophene and/or derivatives thereof; 2-bromo-3-(2-ethylhexyl)thiophene and/or derivatives thereof; 2-bromo-3-octylthiophene and/or derivatives thereof; 3-(2-ethylhexyl)thiophene and/or derivatives thereof; Naphtho[1,2-b:5,6-b']dithiophene and/or derivatives thereof; 2,2'-bithiophene-5-boronic acid pinacol ester and/or derivatives thereof; 5-bromo-5'-hexyl-2,2'-bithiophene and/or derivatives thereof; 5-hexyl-2,2'-bithiophene and/or derivatives thereof; 3,3'-dibromo-5,5'-bis(trimethylsilyl)-2,2'-bithiophene and/or derivatives thereof; 2,5-dibromo-3-decylthiophene and/or derivatives thereof; 5,5'-bis(trimethylstannyl)-2,2'-bithiophene and/or derivatives thereof; 3-decylthiophene and/or derivatives thereof; thiophene-2,5-diboronic acid bis(pinacol) ester and/or derivatives thereof; 2,5-dibromo-3,4-dihexylthiophene and/or derivatives thereof; 2,5-dibromo-3-dodecylthiophene and/or derivatives thereof; 3-hexylthiophene-2-boronic acid pinacol ester and/or derivatives thereof; 5-hexyl-2-thiopheneboronic acid pinacol ester and/or derivatives thereof; 2-bromo-3-dodecylthiophene and/or derivatives thereof; 2-bromo-5-dodecylthiophene and/or derivatives thereof; 3,4-dihexylthiophene and/or derivatives thereof; 3-dodecylthiophene and/or derivatives thereof; 2,2':5',2''-terthiophene-5-boronic acid pinacol ester and/or derivatives thereof; thieno[3,2-b]thiophene-2,5-diboronic acid bis(pinacol ester) and/or derivatives thereof; 2,2'-bithiophene-5,5'-diboronic acid bis(pinacol) ester and/or derivatives thereof; 5'-hexyl-2,2'-bithiophene-5-boronic acid pinacol ester and/or derivatives thereof; 3,3'''-dihexyl-2,2':5',2'':5'',2'''-quaterthiophene and/or derivatives thereof; 5,5'-dibromo-4,4'-didodecyl-2,2'-bithiophene and/or derivatives thereof; 2,6-bis(trimethylstannyl)-4,8-bis(2-ethylhexyloxy)benzo[1,2-b:4,5-b']dithiophene and/or derivatives thereof; 2,6-bis(trimethyltin)-4,8-bis(2-ethylhexyloxy)benzo[1,2-b:4,5-b']dithiophene and/or derivatives thereof; 5,5'-dibromo-4,4'-ditetradecyl-2,2'-bithiophene and/or derivatives thereof; 3,3'''-didodecyl-2,2':5',2'':5'',2'''-quaterthiophene and/or derivatives thereof; 9,9-dioctyl-9H-9-silafluorene-2,7-bis(boronic acid pinacol ester) and/or derivatives thereof; 4,8-bis(3,5-dioctyl-2-thienyl)-2,6-bis(4,4,5,5-tetramethyl-1,3,2-dioxaborolan-2-yl)benzo[1,2-b:4,5-b']dithiophene and/or derivatives thereof; 6,6,12,12-tetrakis(4-hexylphenyl)-6,12-dihydro-dithieno[2,3-d:2',3'-d']-s-indaceno[1,2-b:5,6-b']dithiophene and/or derivatives thereof; 2,8-dibromo-6,12-dihydro-6,6,12,12-tetrakis(4-octylphenyl)-dithieno[2,3-d:2',3'-d']-s-indaceno[1,2-b:5,6-b']dithiophene and/or derivatives thereof; and 6,12-dihydro-6,6,12,12-tetrakis(4-octylphenyl)-2,8-bis(4,4,5,5-tetramethyl-1,3,2-dioxaborolan-2-yl)dithieno[2,3-d:2',3'-d']-s-indaceno[1,2-b:5,6-b']dithiophene and/or derivatives thereof.

The donor compounds can be modified by processes known to those of skill in the art to a boronic acid or a boronic ester for Suzuki cross-coupling reactions (e.g., a pinacol borate), or to a trialkyl stannane (e.g., trimethylstannane) for Stille cross-coupling reactions.

In some embodiments described herein, the acceptor compound may be substituted with an Ar group and an Alkyl' group, for example formula (IV):

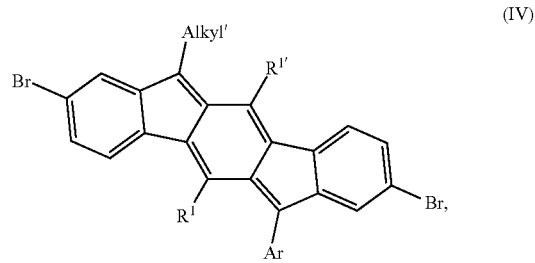

wherein:
each of Alkyl', Ar, $R^1$, and $R^{1'}$ is defined above.

Forming such compounds having an Ar group and Alkyl' group can be performed in a manner similar to the procedures described herein with control of the stoichiometry. Such procedures can be performed by those of skill in the art.

Synthesis of Exemplary Donor-Acceptor Copolymers

FIG. 5A illustrates a general polymerization method 500 of forming a donor-acceptor copolymer 503 (n is an integer from 1 to 100 (such as from about 8 to about 100, such as from about 8 to about 50, such as from about 8 to about 20) according to some embodiments. Any acceptor compound and described herein may participate in this general polymerization method 500. The general polymerization method 500 includes a Suzuki cross-coupling polymerization or a Stille cross-coupling polymerization of an "acceptor" (or electron-poor) compound (e.g., compound 501) with a "donor" (or electron-rich) compound (e.g., compound 502). The donor compound is functionalized with a functional group that allows it to participate in a Suzuki cross-coupling polymerization or a Stille cross-coupling polymerization. Any donor compound known by those skilled in the art may be used such as those comprising a thiophene, for example a modified Benzo[1,2-b:4,5-b']dithiophene-4,8-dione compound 502 where each of W and W' is defined below; and each X is independently a boronic acid or a boronic ester for the Suzuki cross-coupling polymerization (e.g., a pinacol borate), or a trialkyl stannane (e.g., trimethylstannane) for the Stille cross-coupling polymerization. Benzo[1,2-b:4,5-b']dithiophene-4,8-dione may be purchased from Sigma-Aldrich and transformed to a donor compound 502 via methods known to those skilled in the art. In some embodiments, the polymerization is performed to achieve an effective conjugation length of at least about 8 units (n≥8). While not wishing to be bound by theory, the higher the conjugation length, the more the separation of energy levels approach the lower limit for the degree of separation allowed for that donor-acceptor copolymer. As it approaches the lower limit for the degree of separation allowed, the better the donor-acceptor copolymer acts as an organic semiconductor.

If present in 501-503, each of Alkyl, Alkyl', Ar, and Ar' is defined above; and each of W and W' is independently a hydrogen, an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring).

The Stille cross-coupling polymerization typically does not require any additional reagents, though the stoichiometry of donor (e.g., benzodithiophene) to acceptor (IDF) can be tailored to, for example, about 1:1 or about 1:1.05. In some embodiments, the Suzuki cross-coupling polymerization includes a base that can be soluble in a polar solvent. Such bases include a trialkyamine (such as ethyl, butyl, and diisopropyl-ethyl), NaOH, KOH, $CaOH_2$, sodium acetate, various carbonates (such as lithium carbonate, sodium carbonate, potassium carbonate, rubidium carbonate, cesium carbonate), various bicarbonates (such as sodium bicarbonate), sodium tert-butoxide, potassium tert-butoxide, $K_3PO_4$, and para-toluenesulfonate. The Suzuki polymerization can be performed in a variety of solvents such as DMF or in a biphasic system (e.g., water/toluene). In the biphasic systems, a phase transfer agent such as tetrabutylammonium salts or aliquat-336 can be used. Like the Stille cross-coupling polymerization, the stoichiometry of the donor to acceptor in the Suzuki cross-coupling polymerization can be tailored to, for example, about 1:1 or about 1:1.05.

For synthesizing the donor-acceptor small molecules, as described below, the stoichiometry of donor (e.g., the silolodithiophene 522) to acceptor (IDF) is about 2:1 or greater.

Synthesis of Exemplary Donor-Acceptor Small Molecules

FIG. 5B illustrates a general method 510 of forming a donor-acceptor small molecule 513 according to some embodiments. Any acceptor compound described herein may participate in this general method 510. The general method 510 includes a Suzuki cross-coupling reaction or Stille cross-coupling reaction of an acceptor compound (e.g., compound 501) and a "donor/acceptor" (or electron-rich) compound (e.g., compound 512). The donor/acceptor compound is functionalized with a functional group that allows it to participate in a Suzuki cross-coupling or a Stille cross-coupling. By controlling the stoichiometry of the cross-coupling reaction, thiophenes can be added such that $R^4$ and $R^{4'}$ can be the same or different groups. In addition, the donor compounds can have different base structures (e.g., the donor compound 512 and the donor compound 522, shown in FIG. 5C, can be used to react with the acceptor compound 501 to form a donor-acceptor small molecule). Such reactions may be performed by controlling the stoichiometry of the polymerization by methods known to those of skill in the art.

Any "donor/acceptor" compound known by those skilled in the art may be used such as a thiadiazole[3,4-c]pyridine compound 512 where each of $R^4$ and $R^{4'}$ is independently an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring); and X is, e.g., a boronic acid or a boronic ester for Suzuki cross-coupling reactions (e.g., a pinacol borate), or a trialkyl stannane (e.g., trimethylstannane) for Stille cross-coupling reactions. Various thiadiazole[3,4-c]pyridine compounds may be purchased from LabNetwork, Cambridge Mass., and transformed to the donor compound 512 via methods known to those skilled in the art. Other derivatives of the compound have the thiophene group and "X" group swapped positionally—e.g., 7-bromo-4-(thiophen-2-yl)[1,2,5]thiadiazolo[3,4-c]pyridine—which can be purchased commercially from Aquila Pharmatech of Waterville, Ohio or Arch Bioscience Company of West Chester, Pa., and further functionalized to include alkyl groups and/or other functionality.

An example of the thiadiazole[3,4-c]pyridine compound 512 is 4-bromo-7-(5'-hexyl[2,2'-bithiophen]-5-yl)[1,2,5]Thiadiazolo[3,4-c]pyridine, which has two thiophenes instead of one as shown in compound 512.

If present in 501 and 513, each of $R^1$, $R^{1'}$, Alkyl, Alkyl', Ar, Ar', $R^4$, and $R^{4'}$ is defined above.

FIG. 5C illustrates a general method 520 of forming a donor-acceptor small molecule 523 according to some embodiments. Any acceptor compound described above may participate in this general method 520. The general method 520 includes a Suzuki cross-coupling reaction or a Stille cross-coupling reaction of an acceptor compound (e.g., compound 501) and a donor compound (e.g., compound 522). The donor compound is functionalized with a functional group that allows it to participate in a Suzuki cross-coupling or a Stille cross-coupling. By controlling the stoichiometry of the cross-coupling reaction, thiophenes can be added such that $R^5$, $R^{5'}$, $R^6$, $R^{6'}$, $R^7$, and $R^{7'}$ can be the same or different groups. In addition, the donor compounds can have different base structures (e.g., the donor compound 512 and the donor compound 522 can be used to react with the acceptor compound 501 to form a donor-acceptor small molecule). Such reactions may be performed by controlling the stoichiometry of the polymerization by methods known to those of skill in the art.

Any donor compound known by those skilled in the art may be used such as a dithienosilole-thiophene compound. For donor compound 522, $R^5$ and $R^{5'}$ is independently an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical), an alkoxy radical (such as a $C_1$ to $C_{50}$ alkoxy radical, such as a $C_1$ to $C_{20}$ alkoxy radical, such as an ethylene glycol and a polyethylene glycol), a substituted alkoxy radical (such as a $C_1$ to $C_{50}$ substituted alkoxy radical, such as a $C_1$ to $C_{20}$ substituted alkoxy radical, for example a $C_1$ to $C_8$ substituted alkoxy radical), an unsubstituted aryl radical (such as a $C_4$ to $C_{20}$ unsubstituted aryl ring, such as a $C_6$ to $C_{14}$ unsubstituted aryl ring), a substituted aryl radical (such as a $C_4$ to $C_{20}$ substituted aryl ring, such as a $C_6$ to $C_{14}$ substituted aryl ring), an unsubstituted heteroaryl radical (such as a $C_4$ to $C_{20}$ unsubstituted heteroaryl ring, such as a $C_6$ to $C_{14}$ unsubstituted heteroaryl ring), or a substituted heteroaryl radical (such as a $C_4$ to $C_{20}$ substituted heteroaryl ring, such as a $C_6$ to $C_{14}$ substituted heteroaryl ring); each of $R^6$, $R^{6'}$, $R^7$, and $R^{7'}$ is independently an alkyl radical (such as a $C_1$ to $C_{50}$ alkyl radical, such as a $C_1$ to $C_{20}$ alkyl radical, for example a $C_1$ to $C_8$ alkyl radical), a substituted alkyl radical (such as a $C_1$ to $C_{50}$ substituted alkyl radical, such as a $C_1$ to $C_{20}$ substituted alkyl radical, for example a $C_1$ to $C_8$ substituted alkyl radical); and X is, e.g., a boronic acid or a boronic ester for Suzuki cross-coupling reactions (e.g., a pinacol borate), or a trialkyl stannane (e.g., trimethylstannane) for Stille cross-coupling reactions. The dithienosilole-thiophene compound 512 may be synthesized by methods known to those skilled in the art.

If present in 501 and 523, each of $R^1$, $R^{1'}$, Alkyl, Alkyl', Ar, Ar', $R^6$, $R^{6'}$, $R^7$, and $R^{7'}$ is defined above.

In some embodiments, the indenofluorenes, donor-acceptor copolymers, and donor-acceptor small molecules are solution processable n-type organic semiconductors. In some embodiments, the indenofluorenes, donor-acceptor copolymers, and/or donor-acceptor small molecules are incorporated into organic semiconducting devices and fabricated by various solution processing techniques.

The compounds disclosed herein may be used in electronic or electrooptical devices such as an OLED, an OFET, or an OPV cell. Any of the indenofluorenes, donor-acceptor copolymers, and/or donor-acceptor small molecules disclosed herein may be used as organic semiconductors in layers or films, for example, less than about 30 microns thick, such as less than about 5 microns thick, such as less than about 1 micron thick. In some embodiments, and for use in an OFET, the thickness of the layer or film may be about 800 nm or less, such as about 500 nm or less. In some embodiments, and for use in an OLED, the thickness of the layer or film may be about 100 nm or less, such as about 50 nm or less. The exact thickness of the layer will depend, for example, upon the requirements of the electronic device in which the layer is used. In some embodiments, and for use in an OPV, the thickness of the layer or film may be about 100 nm or less, such as about 50 nm or less. The exact thickness of the layer will depend, for example, upon the requirements of the electronic device in which the layer is used.

In some embodiments, the semiconductor channel between the source and drain in an OFET includes a layer or film that includes any indenofluorene described herein, any donor-acceptor copolymer described herein, and/or any donor-acceptor small molecule described herein.

In some embodiments, an OFET may include a source electrode, a drain electrode, a gate electrode, a semiconducting layer, one or more gate insulator layers, optionally a substrate, wherein the semiconductor layer includes any indenofluorene described herein, any donor-acceptor copolymer described herein, and/or any donor-acceptor small molecule described herein.

In some embodiments, a hole injection or transport layer, and/or an electron blocking layer in an OLED device includes a film or layer that includes any indenofluorene described herein, any donor-acceptor copolymer described herein, and/or any donor-acceptor small molecule described herein. In some embodiments, the OLED device includes a hole-blocking layer and/or an electron transport layer.

In some embodiments, an OPV cell includes an anode, a cathode, and a semiconductor layer or film that includes any indenofluorene described herein, any donor-acceptor copolymer described herein, and/or any donor-acceptor small molecule described herein. In some embodiments, the anode material is a transparent material, the material including indium tin oxide, molybdenum oxide materials such as molybdenum dioxide materials and Molybdenum trioxide materials.

Prophetic Procedures

In some embodiments, the aryl-functionalized acceptor compound 202 (which may be made by procedures known in the art) is synthesized by the following prophetic procedure. A solution of a haloarene (e.g., iodobenzene, 2.12 mmol) in tetrahydrofuran (THF, 10 ml) is degassed with argon for about 10 min and cooled to about −78° C. Once cold, n-BuLi (1.6 M in hexanes, 1.77 mmol) is added and the mixture is stirred at about −78° C. for about 20 min to form a lithiate. In a separate flask, the dione 201 (0.35 mmol) is dissolved in THF (30 ml) and degassed with argon for about 10 min, and cooled to about −78° C. Once cold, the lithiate is transferred via cannula to the solution containing the dione, and the mixture is stirred, allowed to warm to room temperature, and monitored for completion by thin layer chromatography. The reaction mixture is then quenched with a 10% HCl solution (30 mL) and extracted in $Et_2O$ (50 mL). The organic layer is dried over $MgSO_4$, filtered, and evaporated to dryness to form a crude diol (not shown). The crude diol is then redissolved in toluene (PhMe, 40 ml) and degassed with argon for about 10 min. To the solution containing the crude diol is added tin(II) chloride ($SnCl_2$, 1.42 mmol) and warmed to about 40° C. while stirring for about 12 hours, and monitored for completion by thin layer chromatography. The solution is then filtered and the filtrate is evaporated to dryness. The crude solid is redissolved in a minimal amount of acetonitrile, filtered once more, and the solid collected. The solvents are removed in vacuo and the crude residue is purified by fractional distillation or column chromatography to produce the aryl-functionalized acceptor compound 202.

In some embodiments, the alkyl-functionalized acceptor compound 204 is synthesized according to the following prophetic procedure. A solution of a (triisopropylsilyl)acetylene (0.76 mmol) in tetrahydrofuran (THF, 10 ml) is degassed with argon for about 10 min and cooled to about −78° C. Once cold, n-BuLi (1.6 M in hexanes, 0.63 mmol) is added and the mixture is stirred at about −78° C. for about 20 min to form a lithiate. In a separate flask, the dione 201 (0.13 mmol) is dissolved in THF (30 ml) and degassed with argon for 10 min, and cooled to about −78° C. Once cold, the lithiate is transferred via cannula to the solution containing the dione, and the reaction mixture is stirred. The reaction mixture is then allowed to warm to room temperature and is monitored for completion by thin layer chromatography. The reaction mixture is then quenched with a 10% HCl solution (30 mL) and extracted in $Et_2O$ (50 mL). The organic layer is dried over $MgSO_4$, filtered, and evaporated to dryness to form a crude diol (not shown). To the solution containing the crude diol is added $SnCl_2$ (1.42 mmol) and warmed to about 40° C. while stirring for about 12 hours, and the reaction is monitored for completion by thin layer chromatography. The solution is then filtered and the filtrate is evaporated to dryness. The crude solid is redissolved in a minimal amount of acetonitrile, filtered once more, and the solid collected. The solvents are removed in vacuo and the crude residue is purified by fractional distillation or column chromatography to produce the di-alkyne compound 203.

According to some embodiments, the di-alkyne compound 203 can be transformed into the alkyl-functionalized acceptor compound 204 in three operations by the following prophetic procedures. To a solution of di-alkyne compound 203 in THF at about 0° C. is added TBAF. The solution is stirred, then allowed to warm to room temperature, and the reaction is monitored for completion by thin layer chromatography. Procedures known in the art for quenching and purification are then performed to give an indenofluorene having two terminal alkynes (not shown). To the newly formed indenofluorene having two terminal alkynes (9.8 mmol) in THF (0.5 M) at about −78° C. is added n-BuLi (1.6 M in hexanes, 9.8 mmol) dropwise within about 10 min, and the mixture is stirred for about 30 min. Then, an alkylhalide, e.g., 5-bromopent-1-ene (11.8 mmol) and N,N-dimethylpropyleneurea (DMPU, 19.6 mmol) is added, and the reaction mixture is stirred for about 2 h at about room temperature. The reaction mixture is then quenched with a saturated solution of ammonium chloride ($NH_4Cl$) and extracted with ethyl acetate, washed with brine, and dried over anhydrous $MgSO_4$. The solvent is removed under vacuum and the alkylated product as a di-alkyne (not shown) is purified by column chromatography (cyclohexane). The hydrogenation operation to form the alkyl-functionalized acceptor compound 204 may be performed by the following prophetic procedure. After two vacuum/$H_2$ cycles to replace the air inside the reaction tube with hydrogen, a mixture of the di-alkyne from the previous alkylation operation (1.00 mmol), Pd/C (10 wt %), in 2:1 THF:ethanol (2.0 mL) is vigorously stirred at room temperature under about 35 bar of hydrogen pressure (using a Parr bomb or a similar style reactor). The reaction is monitored for completion by thin layer chromatography, at which point the reaction mixture is filtered through Celite® or a membrane filter and purified by column chromatography to provide the alkyl-functionalized acceptor compound 204. Alternatively, the hydrogenation can be performed using a flow-process reactor, such as an H-Cube or similar technology. When using the H-Cube reactor, similar amounts of catalyst can be used, the hydrogen pressure is around 100 bar, and the solvent system is 9:1 THF:EtOH.

In some embodiments, the Suzuki cross-coupling to form the dithiophene 205 is performed according to the following prophetic procedure. The dione 201 (11.3 mmol), a thiophene 215 having a boronic ester or a boronic acid (24.9 mmol) and tetrakis(triphenylphosphine)palladium(O) (Pd $(PPh_3)_4$, 0.05 mmol) is dissolved in dry THF (25 ml) under nitrogen. A deaerated solution of $K_2CO_3$ (58 mmol) in THF (25 ml) and water (25 ml) and a few drops of Aliquat 336 are added under nitrogen. The reaction mixture is heated to about 80° C. for about 48 hours under a nitrogen atmosphere, and the reaction is monitored for completion by thin layer chromatography. The organic phase is filtered through a plug of Celite®. Standard procedures for solvent removal and purification are then performed to produce the dithiophene 205.

In some embodiments, the Stille cross-coupling to form dithiophene compound 205 is performed according to the following prophetic procedure. The dione 201 (0.50 mmol) and Pd$(PPh_3)_4$ (0.04 mmol) in toluene is degassed with argon for about 20 min. In a separate flask, a solution of an alkylstannylthiophene, e.g., 2-butyl-5-tributylstannylthiophene (1.2 mmol) in toluene (25 mL) is also degassed for about 20 min. The solution containing the stannane is then transferred by cannula into the first flask and the mixture is refluxed for about 12 h to about 24 h, monitoring by thin layer chromatography. After evaporating the mixture to dryness, the crude material is placed on a plug of Celite® and rinsed with acetonitrile ($CH_3CN$) until the washings were colorless, and then extracted with chloroform ($CHCl_3$) and evaporated to dryness. Standard procedures for purification are then performed to produce the dithiophene 205.

In some embodiments, the aryl-functionalized acceptor compound 207 is synthesized from the dithiophene 205 by the following prophetic procedure. The di-aryl compound 206 is formed by a nucleophilic addition of Ar—Li to the dithiophene 205 to form a diol (not shown), with a subsequent tin chloride reduction of the diol, by procedures similar to those described above. To a stirring solution of the di-aryl compound 206 (94 mmol) in dimethylformamide (DMF, 250 ml) is added N-bromosuccinimide (NBS, 200 mmol) portion-wise. The reaction mixture is stirred for about 5 hours and diluted with H$_2$O (300 ml). The organic layer is extracted with hexane or diethyl ether (3 times). The combined organic layers are washed with 1N NaOH, then washed with H$_2$O, then washed with brine, and then dried over MgSO$_4$. The solvents are removed in vacuo. Standard procedures for isolation and purification (for example, column chromatography) are then performed to provide the aryl-functionalized acceptor compound 207.

In some embodiments, the alkyl-functionalized acceptor compound 211 is synthesized prophetically from the dithiophene 205 by using procedures similar to those described above for the following operations: nucleophilic addition of the alkynyl lithiate; tin chloride reduction; deprotection using TBAF; alkylation of the terminal alkynes; hydrogenation of the alkynes; and bromination. The sequence of such operations can vary. Standard procedures for quenching, solvent removal, isolation, and purification (for example, column chromatography) are performed for these operations, as needed, to provide alkyl-functionalized acceptor compound 211.

In some embodiments, the alkyl-functionalized acceptor compound 306 is synthesized prophetically from the known tetrakis-TIPS alkynyl indenofluorene 301 by using procedures similar to those described above for the following operations: brominations; Suzuki/Stille cross-coupling; deprotection using TBAF; alkylation of the terminal alkynes; and hydrogenation of the alkynes. The sequence of such operations can vary. Standard procedures for quenching, solvent removal, isolation, and purification (for example, column chromatography) are performed, as needed, for these operations to provide the alkyl-functionalized acceptor compound 306.

In some embodiments, the acceptor compound 403 can be synthesized from known di-bromo-dione compound 401 by using procedures similar to those described above for the cross-coupling reactions and the bromination using NBS. Alternately, and in some embodiments, the bromination is performed using liquid bromine (Br$_2$) and a Lewis acid (e.g., iron chloride, FeCl$_3$) as a catalyst by the following prophetic procedure. To a 4-necked flask equipped with a calcium chloride guard tube, a thermometer pocket, and a mechanical stirrer, is charged CHCl$_3$ (50 ml) followed by an anhydrous Lewis acid (e.g., FeCl$_3$, 0.132 mol) under stirring. To this mixture is added the di-bromo-dione compound 401 (0.1 mol) in CHCl$_3$ over a period of about 1 h at about 40° C. After this, Br$_2$ (2.2 mol) is added slowly over a period of about 2 h at about 40° C. The mixture is stirred at about 40° C. for about 2 h while monitoring for completion by thin layer chromatography. The reaction mass is quenched with crushed ice and stirred for about 10 min. The organic layer is separated and is washed with water (100 mL), washed with a 30 ml sodium carbonate solution (5%), and followed by another wash with water (75 mL). The organic extracts are dried with anhydrous MgSO$_4$, and the solvent is removed in vacuo. Standard procedures for isolation and purification (for example, column chromatography) are then performed to provide the acceptor compound 403.

In some embodiments, the Sonogashira cross-coupling to form the bis-TIPS alkynyl indenofluorene 412 from the known dione 411 can be performed according to the following prophetic procedure. To a stirred deoxygenated solution of the dione 411 and (triisopropylsilyl)acetylene in an organic solvent which is an alkylamine (e.g., trimethylamine (Et$_3$N), diethylamine (Et$_2$NH), or diisopropylethalamine (EtN(i-Pr)$_2$)) or a mixture of alkylamine and an organic solvent such as DMF, dichloromethane (DCM), or THF at about 25° C., is added a palladium catalyst (e.g., bis(triphenylphosphine)palladium(II) dichloride (Pd(PPh$_3$)$_2$Cl$_2$) or Pd(PPh$_3$)$_4$) and a copper catalyst (e.g., copper(I) iodide (CuI)). The reaction mixture is heated and maintained at a temperature of about 50° C. to about 80° C. Upon completion of the reaction which is monitored by thin layer chromatography, the solvent is removed in vacuo, and the resulting slurry is subjected to either standard aqueous workup conditions or filtration conditions. The crude product is purified by recrystallization, column chromatography, or by other techniques known in the art to form the bis-TIPS alkynyl indenofluorene 412.

In some embodiments, a Suzuki cross-coupling reaction and/or a Stille cross-coupling reaction to form the di-alkyne compound 208 having thiophene moieties from the di-alkyne compound 203 is performed prophetically by using procedures similar to those described above.

In some embodiments, the donor-acceptor copolymer 503 is synthesized according to the following Stille procedure. An oven-dried, Schlenk flask is charged with dry, deoxygenated toluene or a toluene/DMF mixture 9:1 v/v (5-10 mL), acceptor compound 501 (1.0 equiv.), and a bisstannane-functionalized monomer (donor 502, 1.05 equiv.). The stirred solution is sparged with argon for about 10 minutes and to the stirred solution is added tris(dibenzylideneacetone)dipalladium(O) (2 mol %) and tri(o-tolyl)phosphine (8 mol %). The reaction mixture is heated to reflux and stirred, under argon, for about 4 hours to about 96 hours. The copolymer may be end-capped by the subsequent addition of an excess amount of trimethyl(phenyl)tin and iodobenzene, and each addition may be followed by up to about a 4 hour period of reflux. The reaction mixture is cooled to about 50° C. and is diluted with chloroform. A small portion of SiliaMetS® Cysteine is added to reaction mixture followed by stirring for about 8 hours. The copolymer 503 is precipitated into a cold, organic non-solvent such as methanol, acetone, or hexane and is filtered. The copolymer 503 is purified by any combination of Soxhlet extraction, re-precipitation, filtration, column chromatography or other techniques known to those skilled in the art.

In some embodiments, the donor-acceptor copolymer 503 is synthesized according to the following Suzuki procedure. An oven-dried, Schlenk flask is charged with dry, deoxygenated toluene or toluene/DMF mixture 9:1 v/v, acceptor compound 501 (1.0 equiv.), and a boronic acid/ester functionalized monomer" (donor 502, 1.05 equiv.), aliquat 336 (5-10 mol %/volume), and a deoxygenated 1M K$_2$CO$_3$ solution in water or water/ethanol mixture. The stirred solution is sparged with argon for about 10 minutes and to the stirred solution is added tetrakis(triphenylphosphine) palladium (5 mol %). The reaction mixture is heated to reflux and stirred, under argon, for about 4 to about 96 hours. The polymer may be end-capped by the subsequent addition of an excess amount of phenylboronic acid and iodobenzene, the addition of each may be followed by up to about a 4 hour period of reflux. The organic phase is filtered through a plug of Celite® and evaporated to dryness to give a semi-solid crude product. The semi-solid crude product is then reconstituted in chloroform. The reaction mixture is cooled to about 50° C. and is diluted with chloroform. A small portion of SiliaMetS® Cysteine is added to reaction mixture followed by stirring for about 8 hours. The copolymer 503 is precipitated into a cold, organic non-solvent such as methanol, acetone, or hexane and is filtered. The copolymer 503 is purified by any combination of Soxhlet extraction, re-precipitation, filtration, column chromatography or other techniques known to those skilled in the art.

In some embodiments, the donor-acceptor small molecules 513/523 are synthesized according to the following Stille procedure. An oven-dried, Schlenk flask is charged with dry, deoxygenated toluene or a toluene/DMF mixture 9:1 v/v (5-10 mL), acceptor compound 501 (1.0 equiv.), and a stannane-functionalized compound (donor 512 or 522, 2.0 equiv. or more). The stirred solution is sparged with argon for about 10 minutes and to the stirred solution is added tris(dibenzylideneacetone)dipalladium(O) (2 mol %) and tri(o-tolyl)phosphine (8 mol %). The reaction mixture is heated to reflux and stirred, under argon, for about 4 hours to about 96 hours, monitoring by thin layer chromatography. After evaporating the mixture to dryness, the crude material is placed on a plug of Celite® and rinsed with acetonitrile ($CH_3CN$) until the washings were colorless, and then extracted with chloroform ($CHCl_3$) and evaporated to dryness. Standard procedures for purification are then performed to produce the donor-acceptor small molecules 513/523.

In some embodiments, the donor-acceptor small molecules 513/523 are synthesized according to the following Suzuki procedure. An oven-dried, Schlenk flask is charged with dry, deoxygenated toluene or toluene/DMF mixture 9:1 v/v, acceptor compound 501 (1.0 equiv.), and a boronic acid/ester functionalized compound (donor 512 or 522, 2.0 equiv. or more), aliquat 336 (5-10 mol %/volume), and a deoxygenated 1M $K_2CO_3$ solution in water or water/ethanol mixture. The stirred solution is sparged with argon for about 10 minutes and to the stirred solution is added tetrakis (triphenylphosphine)palladium (5 mol %). The reaction mixture is heated to reflux and stirred, under argon, for about 4 to about 96 hours, and the reaction is monitored for completion by thin layer chromatography. The organic phase is filtered through a plug of Celite®. Standard procedures for solvent removal and purification are then performed to produce donor-acceptor small molecules 513/523.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A method of forming a donor-acceptor small molecule or a donor-acceptor copolymer, comprising:
   forming an indenofluorene, the indenofluorene having the formula

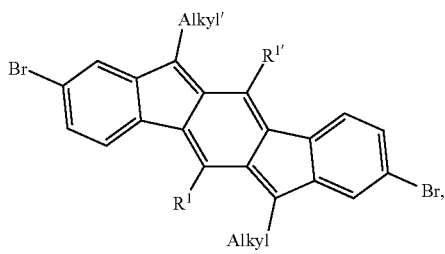

wherein:
   each of $R^1$ and $R^{1'}$ is independently a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring; and
   each of Alkyl and Alkyl' is independently a $C_1$ to $C_{50}$ alkyl radical or a $C_1$ to $C_{50}$ substituted alkyl radical, the $C_1$ to $C_{50}$ alkyl radical and the $C_1$ to $C_{50}$ substituted alkyl radical being linear, branched, or cyclic, and when cyclic, the $C_1$ to $C_{50}$ alkyl radical and the $C_1$ to $C_{50}$ substituted alkyl radical being non-aromatic;
   forming an electron donor; and
   reacting the indenofluorene with the electron donor in a cross-coupling reaction.

2. The method of claim 1, wherein the cross-coupling reaction is a Suzuki cross-coupling reaction, a Suzuki cross-coupling polymerization reaction, a Stille cross-coupling reaction, or a Stille cross-coupling polymerization reaction.

3. The method of claim 1, wherein the cross-coupling reaction is a Stille cross-coupling reaction.

4. The method of claim 1, wherein the electron donor comprises a thiophene.

5. The method of claim 1, wherein the electron donor further comprises a boronic acid, a boronic ester, or a trialkyl stannane.

6. The method of claim 1, wherein the electron donor has the formula

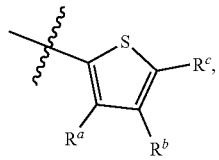

wherein:
   X is a boronic acid, a boronic ester, or a trialkyl stannane; and
   each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

7. The method of claim 1, wherein the electron donor has the formula

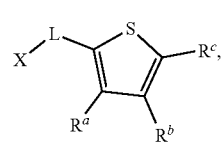

wherein:
L includes at least one carbon atom;
X is a boronic acid, a boronic ester, or a trialkyl stannane; and
each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

8. A method of forming a donor-acceptor small molecule or a donor-acceptor copolymer, comprising:
forming an indenofluorene, the indenofluorene having the formula

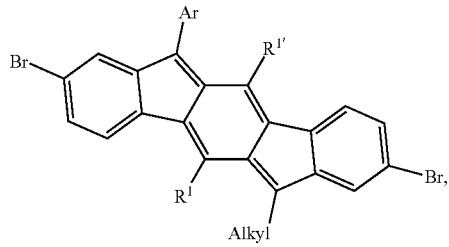

wherein:
each of $R^1$ and $R^{1'}$ is independently a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring;
Ar is a $C_4$ to $C_{20}$ unsubstituted aryl radical, a $C_4$ to $C_{20}$ substituted aryl radical, a $C_4$ to $C_{20}$ unsubstituted heteroaryl radical, or a $C_4$ to $C_{20}$ substituted heteroaryl radical; and
Alkyl is a $C_1$ to $C_{50}$ alkyl radical or a $C_1$ to $C_{50}$ substituted alkyl radical, the $C_1$ to $C_{50}$ alkyl radical and the $C_1$ to $C_{50}$ substituted alkyl radical being linear, branched, or cyclic, and when cyclic, the $C_1$ to $C_{50}$ alkyl radical and the $C_1$ to $C_{50}$ substituted alkyl radical being non-aromatic;
forming an electron donor; and
reacting the indenofluorene with the electron donor in a cross-coupling reaction, wherein the cross-coupling reaction is a Suzuki cross-coupling reaction, a Suzuki cross-coupling polymerization reaction, a Stille cross-coupling reaction, or a Stille cross-coupling polymerization reaction.

9. The method of claim 8, wherein the cross-coupling reaction is the Stille cross-coupling reaction.

10. The method of claim 8, wherein the electron donor comprises a thiophene.

11. The method of claim 8, wherein the electron donor further comprises a boronic acid, a boronic ester, or a trialkyl stannane.

12. The method of claim 8, wherein the electron donor has the formula

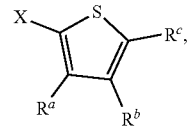

wherein:
X is a boronic acid, a boronic ester, or a trialkyl stannane; and
each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

13. A method of forming a donor-acceptor small molecule or a donor-acceptor copolymer, comprising:
forming an indenofluorene, the indenofluorene having the formula

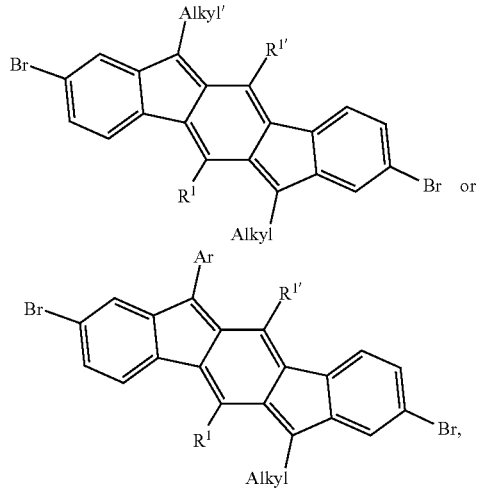

wherein:
each of $R^1$ and $R^{1'}$ is independently a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring;
Ar is a $C_4$ to $C_{20}$ unsubstituted aryl radical, a $C_4$ to $C_{20}$ substituted aryl radical, a $C_4$ to $C_{20}$ unsubstituted heteroaryl radical, or a $C_4$ to $C_{20}$ substituted heteroaryl radical;
Alkyl is a $C_1$ to $C_{50}$ alkyl radical or a $C_1$ to $C_{50}$ substituted alkyl radical, the $C_1$ to $C_{50}$ alkyl radical and the $C_1$ to $C_{50}$ substituted alkyl radical being linear, branched, or cyclic, and when cyclic, the $C_1$ to $C_{50}$ alkyl radical and the $C_1$ to $C_{50}$ substituted alkyl radical being non-aromatic; and when the indenofluorene includes Alkyl', the Alkyl' is a $C_1$ to $C_{50}$ alkyl radical or a $C_1$ to $C_{50}$ substituted alkyl radical, the $C_1$ to $C_{50}$ alkyl radical and the $C_1$ to $C_{50}$ substituted alkyl radical being linear, branched, or cyclic, and when cyclic, the $C_1$ to $C_{50}$ alkyl radical and the $C_1$ to $C_{50}$ substituted alkyl radical being non-aromatic; and reacting the indenofluorene with an electron donor in a cross-coupling reaction, wherein the cross-coupling reaction is a Suzuki cross-coupling reaction, a Suzuki cross-coupling polymerization reaction, a Stille cross-coupling reaction, or a Stille cross-coupling polymerization reaction, wherein the electron donor comprises a thiophene.

14. The method of claim 13, wherein the cross-coupling reaction is the Stille cross-coupling reaction.

15. The method of claim 13, wherein the electron donor further comprises a boronic acid, a boronic ester, or a trialkyl stannane.

16. The method of claim 13, wherein the electron donor has the formula

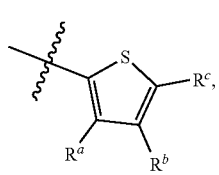

wherein:
X is a boronic acid, a boronic ester, or a trialkyl stannane; and each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

17. The method of claim 8, wherein the electron donor has the formula

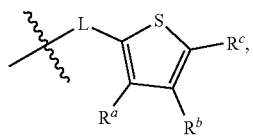

wherein:
L includes at least one carbon atom;
X is a boronic acid, a boronic ester, or a trialkyl stannane; and each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

18. The method of claim 13, wherein the electron donor has the formula

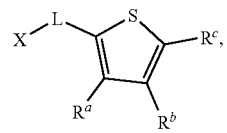

wherein:
L includes at least one carbon atom;
X is a boronic acid, a boronic ester, or a trialkyl stannane; and each of $R^a$, $R^b$, and $R^c$ is independently a hydrogen, a halogen, a $C_1$ to $C_{50}$ alkyl radical, a $C_1$ to $C_{50}$ substituted alkyl radical, a $C_1$ to $C_{50}$ alkoxy radical, a $C_1$ to $C_{50}$ substituted alkoxy radical, a $C_4$ to $C_{20}$ unsubstituted aryl ring, a $C_4$ to $C_{20}$ substituted aryl ring, a $C_4$ to $C_{20}$ unsubstituted heteroaryl ring, or a $C_4$ to $C_{20}$ substituted heteroaryl ring, or one or more of $R^a$ and $R^b$ and $R^b$ and $R^c$ are joined to form a saturated cyclic ring, a substituted saturated cyclic ring, an unsubstituted unsaturated cyclic ring, an unsubstituted saturated cyclic ring, a saturated heterocyclic ring, a substituted saturated heterocyclic ring, an unsubstituted unsaturated heterocyclic ring, or an unsubstituted saturated heterocyclic ring.

19. The method of claim 5, wherein:
the cross-coupling reaction is a Suzuki cross-coupling reaction; and
the electron donor is the boronic acid or the boronic ester.

20. The method of claim 11, wherein:
the cross-coupling reaction is the Suzuki cross-coupling reaction; and
the electron donor is the boronic acid or the boronic ester.

* * * * *